(12) United States Patent
Anizon et al.

(10) Patent No.: US 8,481,586 B2
(45) Date of Patent: Jul. 9, 2013

(54) **PYRROLO[2,3-*A*] CARBAZOLES AND USE THEREOF AS PIM KINASE INHIBITORS**

(75) Inventors: Fabrice Anizon, La Roche-Blanche (FR); Pascale Moreau, Cournon d'Auvergne (FR); Michelle Prudhomme, Clermont-Ferrand (FR); Philip Cohen, Dundee (GB); Bettina Aboab, Clermont-Ferrand (FR); Rufine Akue-Gedu, Clermont-Ferrand (FR); Emilie Rossignol, Saint Amant Tallende (FR)

(73) Assignees: Centre National de la Recherche Scientifique, Paris (FR); Universite Blaise Pascal-Clermont-Ferrand II, Clermont-Ferrand Cedex (FR)

( * ) Notice: Subject to any disclaimer, the term of this patent is extended or adjusted under 35 U.S.C. 154(b) by 202 days.

(21) Appl. No.: 13/002,423

(22) PCT Filed: Jun. 25, 2009

(86) PCT No.: PCT/FR2009/000788
§ 371 (c)(1),
(2), (4) Date: Mar. 10, 2011

(87) PCT Pub. No.: WO2010/000978
PCT Pub. Date: Jan. 7, 2010

(65) Prior Publication Data
US 2011/0263669 A1 Oct. 27, 2011

(30) Foreign Application Priority Data
Jul. 3, 2008 (FR) ...................................... 08 03752

(51) Int. Cl.
*A61K 31/403* (2006.01)
*C07D 209/82* (2006.01)
*C07D 209/86* (2006.01)

(52) U.S. Cl.
USPC ........................................... 514/410; 548/421

(58) Field of Classification Search
None
See application file for complete search history.

(56) References Cited

FOREIGN PATENT DOCUMENTS

WO 2007/044407 4/2007
WO 2007/058942 5/2007

OTHER PUBLICATIONS

Fousteris, et al. J. Het. Chem., 41:349 (2004).*
Fousteris, Pyrrolo[2,3-a]Carbazoles a Potential Cyclin Dependent Kinase 1 (CDK1) Inhibitors. Synthesis Biological Evaluation, and Binding Mode Through Docking Simulations, J. Med. Chem., 51, 2008, 1048-1052.
Pogacic, Structural Analysis Identifies Imidazo[1,2-b]Pyridazines as PIM Kinase Inhibitors with In Vitro Antileukemic Activity, Cancer Res, 67, 2007, 6916-6924.

* cited by examiner

*Primary Examiner* — Michael Barker
(74) *Attorney, Agent, or Firm* — Morgan, Lewis & Bockius LLP

(57) ABSTRACT

The invention relates to pyrrolo[2,3-a]carbazole derivatives, to a method for preparing the same, and to the use thereof as PIM kinase inhibitors. The invention can particularly be used in the pharmaceutical field.

13 Claims, No Drawings

PYRROLO[2,3-A] CARBAZOLES AND USE THEREOF AS PIM KINASE INHIBITORS

RELATED APPLICATIONS

The present application is a U.S. National Phase Application of International Application No. PCT/FR2009/000788 (filed Jun. 25, 2009) which claims priority to French Patent Application No. 0803752 (filed Jul. 3, 2008) which are hereby incorporated by reference in their entirety.

The invention relates to pyrrolo[2,3-a]carbazole derivatives, to a process for preparing them and to the use thereof.

PIM kinase inhibitors are particularly sought on account of their action in the cardiovascular field, on type 2 diabetes, their antiproliferative activity and their potential for inhibiting resistance to certain chemotherapy medicaments.

PIM kinases, i.e. the kinases PIM-1, PIM-2 and PIM-3, are protooncogenes involved in particular in the cancerization process.

They constitute a family of enzymes that plays an important role in regulating many processes, in particular cell survival and transcription regulation and proliferation.

These enzymes are overexpressed in various types of cancer, in particular leukemias, lymphomas and prostate cancers.

These enzymes are also involved in processes of resistance to chemotherapy agents such as rapamycin and growth factor receptor inhibitors with tyrosine kinase activity.

They are targets of choice for the development of novel therapeutic agents, as illustrated in the article by Giles et al., "A PIM kinase inhibitor, please", Blood, 2005, 105, 4158-4159.

Very few specific inhibitors of PIM kinases exist. The term "specific PIM kinase inhibitor" means a compound that strongly inhibits only PIM kinases, and that exerts little or no inhibition on the majority of the other kinases.

The human genome codes for some 500 kinases, and as such the problem of selectivity is crucial.

In general, a compound is said to be a specific inhibitor of a particular type of kinase when it inhibits this type of kinase although it has been tested on at least 30 other kinases.

Many publications describe inhibitors of kinases, including PIM kinases, but these inhibitors are not selective.

The only families of compounds described as being selective for PIM kinases are the following:
- the imidazo[1,2-b]pyridazines described by Pogacic et al. in Cancer Research 2007, 67, 6916-6924,
- quercetagetin described by Holder et al. in Molecular Cancer Therapeutics 2007, 6, 163-172, and
- the ruthenium complexes described by Debreczeni et al. in Angewandte Chemie, Int. Ed., 2006, 45, 1580-1585.

The invention is based on the discovery that certain pyrrolo[2,3-a]-carbazole compounds are selective inhibitors of at least one of the PIM kinases, and that this selectivity is exerted among a panel of 67 tested kinases.

Thus, the invention proposes the use of at least one compound of formula I below:

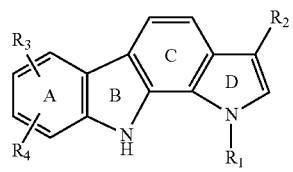

Formula I in which:
$R_1$ is H or a sulfophenyl group,
$R_2$, $R_3$ and $R_4$ are identical or different and represent, independently of each other, a hydrogen atom, a halogen atom or a group from among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —$NR_aR_b$, —$NR_aC(O)$-$T_1$, —C(N—OH)-$T_3$, —C(O)-$T_1$, —C(O)—C(O)-$T_3$, —C(O)—$NR_a$-$T_1$, —$NR_a$—C(O)-$T_1$, —O—C(O)-$T_1$, —C(O)—O-$T_1$, —O-$T_2$-$NR_aR_b$, —O-$T_2$-$OR_a$, —O-$T_2$-$CO_2R_a$, —$NR_a$-$T_2$-$NR_aR_b$, —$NR_a$-$T_2$-$OR_a$, —$NR_a$-$T_2$-$CO_2R_a$ or —$S(O)_t$—$R_a$, —$S(O)_t$—$OR_a$, —$S(O)_t$—$NR_aR_b$, —$P(O)_t$—$R_a$, —$P(O)_t$—$OR_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$,
$R_5$ represents a halogen atom or a group chosen among linear or branched $C_1$ to $C_6$ alkyl, $C_6$ aryl, linear or branched $C_1$ to $C_6$ haloalkyl, —$OR_a$, —$NR_aR_b$, —$CO_2R_a$, —$C(O)R_a$ and —$C(O)NR_aR_b$, nitrile, nitro, —$NR_aC(O)$-$T_1$, $C_1$ to $C_6$ alkoxy, oxo, —$S(O)_t$—$R_a$, —$S(O)_t$—$OR_a$, —$S(O)_t$—$NR_aR_b$, —$P(O)_t$—$R_a$, —$P(O)_t$—$OR_a$,
$R_a$ and $R_b$ are identical or different and represent, independently of each other, a hydrogen atom or a group chosen among linear or branched $C_1$ to $C_6$ alkyl, linear or branched $C_1$ to $C_6$ haloalkyl and $C_6$ aryl, in which $R_a$+$R_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$,
$T_1$ represents a hydrogen atom, a halogen atom or a linear or branched $C_1$ to $C_6$ alkyl group, optionally substituted with a group chosen from —$OR_a$, —$NR_aR_b$, —$CO_2R_a$, —$C(O)R_a$ and —$C(O)NR_aR_b$,
$T_2$ represents a linear or branched ($C_1$-$C_6$)alkylidene chain,
$T_3$ represents a group chosen among -halogen, —$OR_a$, —$NR_aR_b$, —$CO_2R_a$, —$C(O)R_a$ and —$C(O)NR_aR_b$ in which $R_a$ and $R_b$ are as defined previously,
t represents an integer between 0 and 3 inclusive,
A, B, C and D denote the rings constituting the compounds of formula I, and serve merely to identify each of these rings, or a salt, optical isomer or racemic mixture of these compounds, as an inhibitor of the activity of at least one of the kinases PIM-1, PIM-2 or PIM-3.

Preferably, the at least one compound used has the formula I in which:
$R_1$ is H or a sulfophenyl group,
$R_2$ represents H or a group from among CHO, $(CH_2)_nOH$, $C(=O)NH_2$, $C(=O)$—$CF_3$, $(C=O)_2R_c$, $(CH_2)_2NEt_2$, CH(OH)CH₂N(Et)₂, C(NOH)—(C=O)N(Et)₂, NO₂ and Br, with n=1 or 2 and R_c=OCH₃, OC₂H₅, N(C₂H₅)₂, R₃ and R₄ are identical or different and are chosen, independently of each other, from H, a halogen atom, a 5- or 6-membered heteroaryl group comprising one or two heteroatoms chosen from O and N, linear or branched C₁ to C₆ alkyl, methoxy, nitro, nitrile, carboxyl, trifluoromethyl, trifluoromethoxy, SO₂R_d, C₆ aryl optionally substituted with a group chosen from a group (C=O)CH₃, phenyl, methoxy, trifluoromethoxy, trifluoromethyl and carboxyl or with 1 or 2 fluorine atoms, with R_d chosen from a group OH, CH₃ or NH₂.

More preferably, the at least one compound used has the formula I in which:

R₁ is H or a sulfophenyl group,

R₂ represents H or a group from among CHO, (CH₂)_nOH, C(=O)NH₂, C(=O)—CF₃, (CH₂)₂R_c, (CH₂)₂NEt₂, CH(OH)CH₂N(Et)₂, C(NOH)—(C=O)N(Et)₂, NO₂ and Br, with n=1 or 2 and R_c represents a group OCH₃ or OC₂H₅, or N(C₂H₅)₂, R₃ and R₄ are identical or different and are chosen, independently of each other, from H, a halogen atom and a group from among methyl, ethyl, nitro, nitrile, trifluoromethyl, C₆ aryl optionally substituted with a group chosen from a group (C=O)CH₃, phenyl, methoxy, trifluoromethoxy and trifluoromethyl group, or with 1 or 2 fluorine atoms.

Most preferably, the at least one compound of formula I is chosen from 1,10-dihydropyrrolo[2,3-a]carbazole, 1,10-dihydropyrrolo[2,3-a]-carbazole-3-carbaldehyde, 1,10-dihydropyrrolo[2,3-a]carbazole-3-carboxamide, 1-(1,10-dihydropyrrolo[2,3-a]carbazol-3-yl-2,2,2-trifluoroethanone, 7-bromo-1,10-dihydropyrrolo[2,3-a]carbazole, 7-bromo-1,10-dihydropyrrolo[2,3-a]carbazole-3-carbaldehyde, 7-(2,4-difluorophenyl)-1,10-dihydropyrrolo[2,3-a]carbazole-3-carbaldehyde, 6-bromo-1,10-dihydropyrrolo[2,3-a]carbazole-3-carbaldehyde, 9-bromo-1,10-dihydropyrrolo[2,3-a]carbazole-3-carbaldehyde, 7-fluoro-1,10-dihydropyrrolo[2,3-a]carbazole-3-carbaldehyde, 9-fluoro-1,10-dihydropyrrolo[2,3-a]carbazole-3-carbaldehyde, 6,8-dichloro-1,10-dihydropyrrolo[2,3-a]carbazole-3-carbaldehyde, 9-ethyl-1,10-dihydropyrrolo[2,3-a]carbazole-3-carbaldehyde and 8-methyl-1,10-dihydropyrrolo[2,3-a]carbazole-3-carbaldehyde.

Even more preferentially still, the at least one compound of formula I used in the invention is chosen from 1,10-dihydropyrrolo[2,3-a]carbazole, 1,10-dihydropyrrolo[2,3-a]carbazole-3-carbaldehyde, 1,10-dihydropyrrolo[2,3-a]carbazole-3-carboxamide, 1-(1,10-dihydropyrrolo[2,3-a]-carbazol-3-yl-2,2,2-trifluoroethanone, 7-bromo-1,10-dihydropyrrolo[2,3-a]-carbazole, 7-bromo-1,10-dihydropyrrolo[2,3-a]carbazole-3-carbaldehyde, 7-(2,4-difluorophenyl)-1,10-dihydropyrrolo[2,3-a]carbazole-3-carbaldehyde, 6-bromo-1,10-dihydropyrrolo[2,3-a]carbazole-3-carbaldehyde, 9-bromo-1,10-dihydropyrrolo[2,3-a]carbazole-3-carbaldehyde, 7-fluoro-1,10-dihydropyrrolo[2,3-a]carbazole-3-carbaldehyde, 9-fluoro-1,10-dihydropyrrolo[2,3-a]carbazole-3-carbaldehyde, 6,8-dichloro-1,10-dihydropyrrolo[2,3-a]carbazole-3-carbaldehyde, 9-ethyl-1,10-dihydropyrrolo[2,3-a]carbazole-3-carbaldehyde and 8-methyl-1,10-dihydropyrrolo[2,3-a]carbazole-3-carbaldehyde.

The invention also proposes a process for synthesizing the compounds of formula I below:

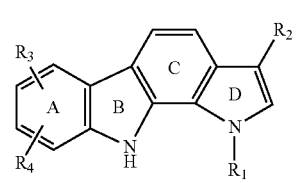

Formula I in which:

R₁ is H or a sulfophenyl group,

R₂, R₃ and R₄ are identical or different and represent, independently of each other, a hydrogen atom, a halogen atom or a group chosen among nitro, nitrile, hydroxyl, linear or branched C₁ to C₆ alkoxy optionally substituted with one or more groups R₅, C₅ to C₆ cycloalkoxy optionally substituted with one or more groups R₅, 5- or 6-membered heterocycloalkoxy optionally substituted with one or more groups R₅, —SH, linear or branched C₁ to C₆ alkylthio optionally substituted with one or more groups R₅, C₆ aryl optionally substituted with one or more groups R₅, C₆ aryloxy optionally substituted with one or more groups R₅, —NR_aR_b, —NR_aC(O)-T₁, —C(N—OH)-T₃, —C(O)-T₁, —C(O)—C(O)-T₃, —C(O)—NR_a-T₁, —NR_a—C(O)-T₁, —O—C(O)-T₁, —C(O)—O-T₁, —O-T₂-NR_aR_b, —O-T₂-OR_a, —O-T₂CO₂R_a, —NR_a-T₂-NR_aR_b, —NR_a-T₂-OR_a, —NR_a-T₂-CO₂R_a or —S(O)_t—R_a, —S(O)_t—OR_a, —S(O)_t—NR_aR_b, —P(O)_t—R_a, —P(O)_t—OR_a, linear or branched C₁ to C₆ alkyl optionally substituted with one or more groups R₅, linear or branched C₁ to C₆ alkenyl optionally substituted with one or more groups R₅, linear or branched C₁ to C₆ alkynyl optionally substituted with one or more groups R₅, 5- or 6-membered heteroaryl optionally substituted with one or more groups R₅, 5- or 6-membered heterocycloalkyl optionally substituted with one or more groups R₅, 5- or 6-membered heteroaryloxy optionally substituted with one or more groups R₅, R₅ represents a halogen atom or a group from among linear or branched C₁ to C₆ alkyl, C₆ aryl, linear or branched C₁ to C₆ haloalkyl, —OR_a, —NR_aR_b, —CO₂R_a, —C(O)R_a and —C(O)NR_aR_b, nitrile, nitro, —NR_aC(O)-T₁, C₁ to C₆ alkoxy, oxo, —S(O)_t—R_a, —S(O)_t—OR_a, —S(O)_t—NR_aR_b, —P(O)_t—R_a, —P(O)_t—OR_a, R_a and R_b are identical or different and represent, independently of each other, a hydrogen atom or a group chosen among linear or branched C₁ to C₆ alkyl, linear or branched C₁ to C₆ haloalkyl and C₆ aryl, in which R_a+R_b form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups R₅, T₁ represents a hydrogen atom, a halogen atom or a linear or branched C₁ to C₆ alkyl group, optionally substituted with a group chosen from —OR_a, —NR_aR_b, —CO₂R_a, —C(O)R_a and —C(O)NR_aR_b, T₂ represents a linear or branched (C₁-C₆)alkylidene chain, T₃ represents a group chosen from -halogen, —OR_a, —NR_aR_b, —CO₂R_a, —C(O)R_a and —C(O)NR_aR_b in which R_a and R_b, are as defined previously, t represents an integer between 0 and 3 inclusive, A, B, C and D denote the rings constituting the compounds of formula I, and serve merely to identify each of these rings, characterized in that it comprises a Fischer indolization of the compound 1-benzenesulfonyl-1,4,5,6-tetrahydro-7H-indol-7-one of formula II below:

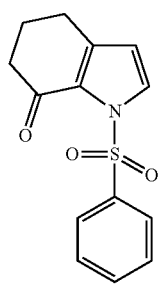

Formula II and of phenylhydrazine or of phenylhydrazine substituted on the phenyl with one or more groups $R_5$, in the presence of an ionic liquid, which is 2/1 zinc chloride-choline chloride of formula III below:

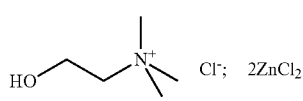

Formula III

The invention also proposes compounds of formula I below:

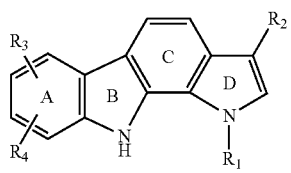

in which:

$R_1$ is H or a sulfophenyl group, $R_2$, $R_3$ and $R_4$ are identical or different and represent, independently of each other, a hydrogen atom, a halogen atom or a group chosen among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —$NR_aR_b$, —$NR_aC(O)$-$T_1$, —C(N—OH)-$T_3$, —C(O)-$T_1$, —C(O)—C(O)-$T_3$, —C(O)—$NR_a$-$T_1$, —$NR_a$—C(O)-$T_1$, —O—C(O)-$T_1$, —C(O)—O-$T_1$, —O-$T_2$-$NR_aR_b$, —O-$T_2$-$OR_a$, —O-$T_2CO_2R_a$, —$NR_a$-$T_2$-$NR_aR_b$, —$NR_a$-$T_2$-$OR_a$, —$NR_a$-$T_2$-$CO_2R_a$ or —$S(O)_t$—$R_a$, —$S(O)_t$—$OR_a$, —$S(O)_t$—$NR_aR_b$, —$P(O)_t$—$R_a$, —$P(O)_t$—$OR_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$, $R_5$ represents a halogen atom or a group chosen among linear or branched $C_1$ to $C_6$ alkyl, $C_6$ aryl, linear or branched $C_1$ to $C_6$ haloalkyl, —$OR_a$, —$NR_aR_b$, —$CO_2R_a$, —$C(O)R_a$ and —$C(O)NR_aR_b$, nitrile, nitro, —$NR_aC(O)$-$T_1$, $C_1$ to $C_6$ alkoxy, oxo, —$S(O)_t$—$R_a$, —$S(O)_t$—$OR_a$, —$S(O)_t$—$NR_aR_b$, —$P(O)_t$—$R_a$, —$P(O)_t$—$OR_a$, $R_a$ and $R_b$ are identical or different and represent, independently of each other, a hydrogen atom or a group from among linear or branched $C_1$ to $C_6$ alkyl, linear or branched $C_1$ to $C_6$ haloalkyl and $C_6$ aryl, in which $R_a$+$R_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$, $T_1$ represents a hydrogen atom, a halogen atom or a linear or branched $C_1$ to $C_6$ alkyl group, optionally substituted with a group chosen from —$OR_a$, —$NR_aR_b$, —$CO_2R_a$, —$C(O)R_a$ and —$C(O)NR_aR_b$, $T_2$ represents a linear or branched ($C_1$-$C_6$)alkylidene chain, $T_3$ represents a group chosen from -halogen, —$OR_a$, —$NR_aR_b$, —$CO_2R_a$, —$C(O)R_a$ and —$C(O)NR_aR_b$ in which $R_a$ and $R_b$ are as defined previously, t represents an integer between 0 and 3 inclusive, A, B, C and D denote the rings constituting the compounds of formula I, and serve merely to identify each of these rings, at the provisos:

$R_1$, $R_2$, $R_3$ and $R_4$ are not all simultaneously H, when $R_1$ is a sulfophenyl group, then $R_2$, $R_3$ and $R_4$ are not all simultaneously H, and when $R_2$ is a carboxamide or formyl group, then $R_1$, $R_3$ and $R_4$ are not all simultaneously H.

Preferably, these compounds have the formula I in which:

$R_1$ is H or a sulfophenyl group, $R_2$ represents H, or a group chosen among CHO, $(CH_2)_n$OH, $C(=O)NH_2$, $C(=O)$—$CF_3$, $(C=O)_2R_c$, $(CH_2)_2NEt_2$, $CH(OH)CH_2N(Et)_2$, $C(NOH)$—$(C=O)N(Et)_2$, $NO_2$ and Br with n=1 or 2 and $R_c$=$OCH_3$, $OC_2H_5$ or $N(C_2H_5)_2$, $R_3$ and $R_4$ are identical or different and are chosen, independently of each other, from H, a halogen atom, a 5- or 6-membered heteroaryl group comprising one or two heteroatoms chosen from O and N, linear or branched $C_1$ to $C_6$ alkyl, methoxy, nitro, nitrile, carboxyl, trifluoromethyl, trifluoromethoxy, $SO_2R_d$, $C_6$ aryl optionally substituted with a group chosen from a group $(C=O)CH_3$, phenyl, methoxy trifluoromethoxy, trifluoromethyl and carboxyl or with 1 or 2 fluorine atoms, with $R_d$ chosen from a group OH, $CH_3$ or $NH_2$.

More preferably, these compounds have the formula I in which:

$R_1$ is H or a sulfophenyl group, $R_2$ represents H or a group from among CHO, $(CH_2)_n$OH, $C(=O)NH_2$, $C(O)$—$CF_3$, $(C=O)_2R_c$, $(CH_2)_2NEt_2$, CH(OH)CH₂N(Et)₂, C(NOH)—(C=O)N(Et)₂, NO₂ and Br, with n=1 or 2 and R_c represents a group OCH₃, OC₂H₅ or N(C₂H₅)₂, R₃ and R₄ are identical or different and are chosen, independently of each other, from H, a halogen atom and a group chosen among methyl, ethyl, nitro, nitrile, trifluoromethyl, C₆ aryl optionally substituted with a group chosen from a group (C=O)CH₃, phenyl, methoxy, trifluoromethoxy and trifluoromethyl, or with 1 or 2 fluorine atoms.

Even more preferably, the compounds of formula I are chosen from:
(1,10-dihydropyrrolo[2,3-a]carbazol-3-yl)methanol,
1-(1,10-dihydropyrrolo[2,3-a]carbazol-3-yl)-2,2,2-trifluoroethanone,
methyl 2-(1,10-dihydropyrrolo[2,3-a]carbazol-3-yl)-2-oxoacetate,
ethyl 2-(1,10-dihydropyrrolo[2,3-a]carbazol-3-yl)-2-oxoacetate,
2-(1,10-dihydropyrrolo[2,3-a]carbazol-3-yl)ethanol,
2-(1,10-dihydropyrrolo[2,3-a]carbazol-3-yl)-N,N-diethyl-2-oxoacetamide,
2-(1,10-dihydropyrrolo[2,3-a]carbazol-3-yl)-N,N-diethylethanamine,
1-(1,10-dihydropyrrolo[2,3-a]carbazol-3-yl)-2-diethylaminoethanol,
2-(1,10-dihydropyrrolo[2,3-a]carbazol-3-yl)-N,N-diethyl-2-hydroxy-iminoethanamide,
1-benzenesulfonyl-7-bromo-1,10-dihydropyrrolo[2,3-a]carbazole,
7-bromo-1,10-dihydropyrrolo[2,3-a]carbazole,
7-bromo-1,10-dihydropyrrolo[2,3-a]carbazole-3-carbaldehyde,
7-(4-acetylphenyl)-1,10-dihydropyrrolo[2,3-a]carbazole,
7-(3-methoxyphenyl)-1,10-dihydropyrrolo[2,3-a]carbazole,
7-(4-biphenyl)-1,10-dihydropyrrolo[2,3-a]carbazole,
7-phenyl-1,10-dihydropyrrolo[2,3-a]carbazole,
7-(4-fluorophenyl)-1,10-dihydropyrrolo[2,3-a]carbazole,
7-(2,4-difluorophenyl)-1,10-dihydropyrrolo[2,3-a]carbazole,
7-(4-trifluoromethylphenyl)-1,10-dihydropyrrolo[2,3-a]carbazole,
7-(4-trifluoromethoxyphenyl)-1,10-dihydropyrrolo[2,3-a]carbazole,
8-bromo-1,10-dihydropyrrolo[2,3-a]carbazole,
6-bromo-1,10-dihydropyrrolo[2,3-a]carbazole,
9-bromo-1,10-dihydropyrrolo[2,3-a]carbazole,
7-fluoro-1,10-dihydropyrrolo[2,3-a]carbazole,
9-fluoro-1,10-dihydropyrrolo[2,3-a]carbazole,
6,8-dichloro-1,10-dihydropyrrolo[2,3-a]carbazole,
1,10-dihydropyrrolo[2,3-a]carbazole-7-carbonitrile,
7-nitro-1,10-dihydropyrrolo[2,3-a]carbazole,
9-ethyl-1,10-dihydropyrrolo[2,3-a]carbazole,
9-(trifluoromethyl)-1,10-dihydropyrrolo[2,3-a]carbazole,
8-methyl-1,10-dihydropyrrolo[2,3-a]carbazole,
7-(3-methoxyphenyl)-1,10-dihydropyrrolo[2,3-a]carbazole-3-carbaldehyde,
7-(4-biphenyl)-1,10-dihydropyrrolo[2,3-a]carbazole-3-carbaldehyde,
7-phenyl-1,10-dihydropyrrolo[2,3-a]carbazole-3-carbaldehyde,
7-(4-fluorophenyl)-1,10-dihydropyrrolo[2,3-a]carbazole-3-carbaldehyde,
7-(2,4-difluorophenyl)-1,10-dihydropyrrolo[2,3-a]carbazole-3-carbaldehyde,
7-(4-trifluoromethylphenyl)-1,10-dihydropyrrolo[2,3-a]carbazole-3-carbaldehyde,
7-(4-trifluoromethoxyphenyl)-1,10-dihydropyrrolo[2,3-a]carbazole-3-carbaldehyde,
8-bromo-1,10-dihydropyrrolo[2,3-a]carbazole-3-carbaldehyde,
6-bromo-1,10-dihydropyrrolo[2,3-a]carbazole-3-carbaldehyde,
9-bromo-1,10-dihydropyrrolo[2,3-a]carbazole-3-carbaldehyde,
7-fluoro-1,10-dihydropyrrolo[2,3-a]carbazole-3-carbaldehyde,
9-fluoro-1,10-dihydropyrrolo[2,3-a]carbazole-3-carbaldehyde,
6,8-dichloro-1,10-dihydropyrrolo[2,3-a]carbazole-3-carbaldehyde,
3-formyl-1,10-dihydropyrrolo[2,3-a]carbazole-7-carbonitrile,
7-nitro-1,10-dihydropyrrolo[2,3-a]carbazole-3-carbaldehyde,
9-ethyl-1,10-dihydropyrrolo[2,3-a]carbazole-3-carbaldehyde,
8-methyl-1,10-dihydropyrrolo[2,3-a]carbazole-3-carbaldehyde.

The compounds of the invention that are the most preferred are 1,10-dihydropyrrolo[2,3-a]carbazol-3-yl-2,2,2-trifluoroethanone, 7-bromo-1,10-dihydropyrrolo[2,3-a]carbazole, 7-bromo-1,10-dihydropyrrolo[2,3-a]-carbazole-3-carbaldehyde, 7-(2,4-difluorophenyl)-1,10-dihydropyrrolo[2,3-a]carbazole-3-carbaldehyde, 6-bromo-1,10-dihydropyrrolo[2,3-a]carbazole-3-carbaldehyde, 9-bromo-1,10-dihydropyrrolo[2,3-a]carbazole-3-carbaldehyde, 7-fluoro-1,10-dihydropyrrolo[2,3-a]carbazole-3-carbaldehyde, 9-fluoro-1,10-dihydropyrrolo[2,3-a]carbazole-3-carbaldehyde, 6,8-dichloro-1,10-dihydropyrrolo[2,3-a]carbazole-3-carbaldehyde, 9-ethyl-1,10-dihydropyrrolo[2,3-a]carbazole-3-carbaldehyde and 8-methyl-1,10-dihydropyrrolo[2,3-a]carbazole-3-carbaldehyde.

The invention will be understood more clearly and other advantages and characteristics thereof will emerge more clearly on reading the explanatory description that follows.

The invention is based on the discovery that the compounds having the formula I below:

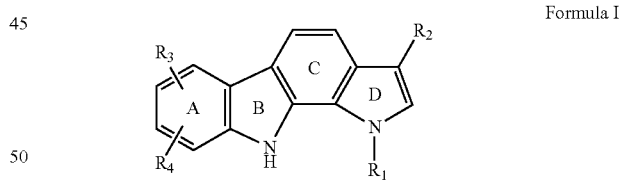

Formula I in which:
R₁ is H or a sulfophenyl group,
R₂, R₃ and R₄ are identical or different and represent, independently of each other, a hydrogen atom, a halogen atom or a group chosen among nitro, nitrile, hydroxyl, linear or branched C₁ to C₆ alkoxy optionally substituted with one or more groups R₅, C₅ to C₆ cycloalkoxy optionally substituted with one or more groups R₅, 5- or 6-membered heterocycloalkoxy optionally substituted with one or more groups R₅, —SH, linear or branched C₁ to C₆ alkylthio optionally substituted with one or more groups R₅, C₆ aryl optionally substituted with one or more groups R₅, C₆ aryloxy optionally substituted with one or more groups R₅, —NR_aR_b, —NR_aC(O)-T₁, —C(N—OH)-T₃, —C(O)-T₁, —C(O)—C(O)-T₃, —C(O)—NR$_a$-T$_1$, —NR$_a$—C(O)-T$_1$, —O—C(O)-T$_1$, —C(O)—O-T$_1$, —O-T$_2$-NR$_a$R$_b$, —O-T$_2$-OR$_a$, —O-T$_2$-CO$_2$R$_a$, —NR$_a$-T$_2$-NR$_a$R$_b$, —NR$_a$-T$_2$-OR$_a$, —NR$_a$-T$_2$-CO$_2$R$_a$ or —S(O)$_t$—R$_a$, —S(O)$_t$—OR$_a$, —S(O)$_t$—NR$_a$R$_b$, —P(O)$_t$—R$_a$, —P(O)$_t$—OR$_a$, linear or branched C$_1$ to C$_6$ alkyl optionally substituted with one or more groups R$_5$, linear or branched C$_1$ to C$_6$ alkenyl optionally substituted with one or more groups R$_5$, linear or branched C$_1$ to C$_6$ alkynyl optionally substituted with one or more groups R$_5$, 5- or 6-membered heteroaryl optionally substituted with one or more groups R$_5$, 5- or 6-membered heterocycloalkyl optionally substituted with one or more groups R$_5$, 5- or 6-membered heteroaryloxy optionally substituted with one or more groups R$_5$, R$_5$ represents a halogen atom or a group chosen among linear or branched C$_1$ to C$_6$ alkyl, C$_6$ aryl, linear or branched C$_1$ to C$_6$ haloalkyl, —OR$_a$, —NR$_a$R$_b$, —CO$_2$R$_a$, —C(O)R$_a$ and —C(O)NR$_a$R$_b$, nitrile, nitro, —NR$_a$C(O)-T$_1$, C$_1$ to C$_6$ alkoxy, oxo, —S(O)$_t$—R$_a$, —S(O)$_t$—OR$_a$, —S(O)$_t$—NR$_a$R$_b$, —P(O)$_t$—R$_a$, —P(O)$_t$—OR$_a$, R$_a$ and R$_b$ are identical or different and represent, independently of each other, a hydrogen atom or a group from among linear or branched C$_1$ to C$_6$ alkyl, linear or branched C$_1$ to C$_6$ haloalkyl and C$_6$ aryl, in which R$_a$+R$_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups R$_5$, T$_1$ represents a hydrogen atom, a halogen atom or a linear or branched C$_1$ to C$_6$ alkyl group, optionally substituted with a group chosen from —OR$_a$, —NR$_a$R$_b$, —CO$_2$R$_a$, —C(O)R$_a$ and —C(O)NR$_a$R$_b$, T$_2$ represents a linear or branched (C$_1$-C$_6$)alkylidene chain, T$_3$ represents a group chosen from -halogen, —OR$_a$, —NR$_a$R$_b$, —CO$_2$R$_a$, —C(O)R$_a$ and —C(O)NR$_a$R$_b$ in which R$_a$ and R$_{ic}$, are as defined previously, t represents an integer between 0 and 3 inclusive, A, B, C and D denote the rings constituting the compounds of formula I, and serve merely to identify each of these rings, are selective inhibitors of at least one kinase PIM-1, PIM-2 or PIM-3 when tested on 67 kinases.

Due to their properties of selective inhibition of at least one kinase PIM-1, PIM-2 or PIM-3, they have particularly advantageous properties in the anticancer field. These compounds may be used either alone or as a therapeutic combination, in particular with other anticancer agents, for instance paclitaxel, tamoxifen and derivatives thereof, cisplatin and analogs thereof, irinotecan and metabolites thereof, various alkylating agents, etoposide, Vinca alkaloids, anthracyclines, nitrosoureas, hormone therapy and radiotherapy.

These compounds of formula I may be used in their native form or in the form of optical isomers thereof or in the form of a racemic mixture of these optical isomers or of an addition salt of these compounds of formula I with a pharmaceutically acceptable acid or base.

The preferred, more preferred, most preferred and even more preferred compounds of formula I used as selective inhibitors of at least one kinase PIM-1, PIM-2 or PIM-3 have been defined above.

When the group R$_2$, R$_3$ and/or R$_4$ is a group that is itself substituted with one or more groups R$_5$, it is preferably substituted with at least two groups R$_5$.

When the group R$_2$, R$_3$ and/or R$_4$ is a group that is itself substituted with two groups R$_5$, then the two groups R$_5$ are preferably identical.

Certain compounds of formula I have already been described. These are compounds in which R$_1$, R$_2$, R$_3$ and R$_4$ are all simultaneously H, compounds in which R$_1$ is a sulfophenyl group and R$_2$, R$_3$ and R$_4$ are all simultaneously H, and compounds in which R$_2$ is a carboxamide group or a formyl group and R$_1$, R$_3$ and R$_4$ are all simultaneously H.

However, these compounds have never been described as selective inhibitors of at least one kinase PIM-1, PIM-2 or PIM-3. Nor has it ever been reported, before the invention, that they could be such inhibitors, and all the less so with such selectivity.

On the other hand, the compounds of formula I in which R$_1$, R$_2$, R$_3$ and R$_4$ are not all simultaneously H or in which R$_1$ is a sulfophenyl group but in which R$_2$, R$_3$ and R$_4$ are not all simultaneously H, or alternatively in which R$_2$ is a carboxamide group or a formyl group, but in which R$_1$, R$_3$ and R$_4$ are not all simultaneously H, have never been described previously.

These compounds are thus a subject of the invention.

Such preferred, more preferred and most preferred compounds have been described previously.

The invention also proposes a process for manufacturing the compounds of formula I, which may be used as an alternative to the standard process for manufacturing these pyrrolo[2,3-a]carbazole derivatives.

This process comprises a Fischer indolization reaction of 1-benzenesulfonyl-1,4,5,6-tetrahydro-7H-indol-7-one with phenylhydrazine or a phenylhydrazine substituted on the phenyl with one or more groups R$_5$, in the presence of an ionic liquid, 2/1 zinc chloride-choline chloride.

In order to have the invention more clearly understood, several embodiments thereof will be described, as purely illustrative and non-limiting examples.

I) EXAMPLES OF SYNTHESES

The structures of the compounds described in the examples that follow are determined according to usual techniques (infrared spectrometry, mass spectrometry, nuclear magnetic resonance spectrometry, etc.). In the nuclear magnetic resonance spectrometry data, the abbreviation "bs" means a broadered signal.

Preparation A: synthesis of 1-benzenesulfonylpyrrole

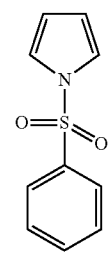

1-Benzenesulfonylpyrrole serves to prepare 1-benzenesulfonyl-1,4,5,6-tetrahydro-7H-indol-7-one, which will be used for the synthesis of the compounds according to the invention.

This compound is obtained according to the process described by B. P. Smart et al. in J. Med. Chem., 2006, 49, 2858-2860.

Preparation B: synthesis of 1-benzenesulfonyl-1,4,5,6-tetrahydro-7H-indol-7-one

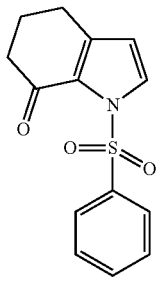

Formula II

This product is obtained according to the process described by M. Kakushima et al. in J. Org. Chem., 1983, 48, pp. 3214-3219.

Preparation C: Preparation of the Ionic Liquid 2/1 Zinc Chloride-Choline Chloride

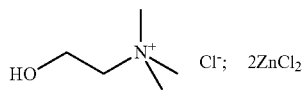

Formula III

A mixture of choline chloride (10.0 g; 71.6 mmol) and zinc chloride (19.5 g; 143 mmol) in toluene (200 mL) is refluxed in Dean-Stark apparatus with vigorous stirring for 15 hours. After cooling and separation of the phases by settling, the ionic liquid is obtained in the form of a yellow oil. The ionic liquid, which is highly hygroscopic, may be used directly, or stored under argon in anhydrous ether.

Example 1

1-benzenesulfonyl-1,10-dihydropyrrolo[2,3-a]carbazole

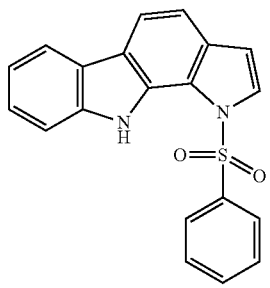 [SMILES: O=S(=O)(c1ccccc1)n1ccc2ccc3c4ccccc4[nH]c3c21]

Method 1:
Stage A:
A solution of the compound of Preparation B (9.65 g; 35.0 mmol) and of phenylhydrazine (6.92 mL; 70.3 mmol) in nitromethane (360 mL) is stirred for 3 hours at reflux.

Stage B:
$P_2O_5$ (9.91 g; 69.8 mmol) is added to a solution of hexamethyldisiloxane (23.9 mL; 112 mmol) in dichloromethane (350 mL) and the mixture is then stirred at reflux for 40 minutes. The solvent is removed by distillation and the residual liquid is heated at 180° C. for 5 minutes. The oil obtained (PPSE) is diluted in nitromethane (180 mL) and the solution is transferred into the preparation obtained from the preceding stage. The mixture is refluxed with stirring for 6 hours, and DDQ (3.50 g; 15.4 mmol) is then added. The mixture is stirred at room temperature for 12 hours and then filtered through Celite and concentrated under vacuum. $Et_2O$ is then added to the residue and the solution is filtered through silica. The filtrate is concentrated and then purified by chromatography on a column of flash silica (eluent: 9/1 cyclohexane/$Et_2O$). After evaporation, the solid obtained is washed with methanol (20 mL) and then with $Et_2O$ (2×50 mL) to give the desired compound (4.40 g; 12.7 mmol; yield=36%) in the form of a beige-colored solid.

Method 2:
A mixture of phenylhydrazine (393 mg; 3.63 mmol), the compound of Preparation B (500 mg; 1.82 mmol) and the ionic liquid of Preparation C (5.25 g; 12.7 mmol) is stirred at 120° C. for 2 hours. The brown oil obtained is cooled and aqueous 0.5 M HCl solution is added. The mixture is extracted with ethyl acetate (3×50 mL). The combined organic phases are washed with saturated aqueous NaCl solution, dried over $MgSO_4$ and filtered. The solution obtained contains the indolization product, as the major product, and the expected product, as the minor product.

DDQ (0.29 g; 1.28 mmol; the necessary amount of DDQ is determined from the $^1H$ NMR spectrum of the intermediate mixture) is added to this solution and the mixture is stirred at room temperature for 15 hours. The mixture is washed with saturated aqueous NaCl solution, dried over $MgSO_4$, filtered and then concentrated on silica, followed by purification by chromatography on flash silica gel (95/5 and then 90/10 pentane/ethyl acetate) to give the expected compound (0.49 g; 1.41 mmol; yield=78%) in the form of a white solid.

Melting point: 148° C.
IR (KBr): 3430, 1630, 1610 $cm^{-1}$
High resolution mass spectrum (ESI+): calculated for $C_{20}H_{15}N_2O_2S$ (M+H)$^+$347.0854. found 347.0861.
$^1H$ NMR (400 MHz, DMSO-$d_6$): 6.85 (1H, d, J=3.5 Hz); 7.28-7.39 (4H, m); 7.44-7.52 (2H, m); 7.53 (1H, d, J=3.5 Hz); 7.64 (1H, d, J=8.0 Hz); 7.75-7.80 (2H, m); 8.01 (1H, d, J=8.0 Hz); 8.12 (1H, d, J=8.0 Hz); 10.12 (1H, bs, NH)
$^{13}C$ NMR (100 MHz, DMSO-$d_6$): 111.4; 112.6; 113.0; 117.1; 119.9 (2C); 125.5; 126.1; 126.7 (2C); 129.5 (2C); 133.9 (CH); 120.4; 121.9; 123.8; 127.0; 130.6; 137.9; 138.8 (C)

Example 2

1,10-dihydropyrrolo[2,3-a]carbazole

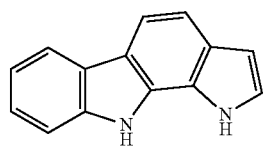 [SMILES: c1ccc2c(c1)[nH]c1c2ccc2cc[nH]c21]

Aqueous 5M NaOH solution (125 mL) is added to a suspension of the compound of Example 1 (3.12 g; 9.0 mmol) in methanol (1.0 L). The mixture is stirred at reflux for 12 hours. The reaction mixture is concentrated under vacuum until a precipitate forms, which is recovered by filtration. The solid obtained is washed with MeOH (10 mL) and then with Et$_2$O (2×30 mL) to give the expected compound (1.71 g; 8.3 mmol; yield=92%) in the form of an off-white solid.

Melting point: 295° C.

IR (KBr): 3420, 3385, 1650, 1455, 1445, 1395, 1345, 1310 cm$^{-1}$

High resolution mass spectrum (ESI+): calculated for $C_{14}H_{11}N_2$ (M+H)$^+$ 207.0922. found 207.0925.

$^1$H NMR (400 MHz, DMSO-d$_6$): 6.61 (1H, dd, $J_1$=3.0 Hz, $J_2$=2.0 Hz); 7.18 (1H, ddd, $J_1$=8.0 Hz, $J_2$=7.0 Hz, $J_3$=1.0 Hz); 7.33 (1H, ddd, $J_1$=8.0 Hz, $J_2$=7.0 Hz, $J_3$=1.0 Hz); 7.37 (1H, d, J=8.5 Hz); 7.42 (1H, t, J=3.0 Hz); 7.64 (1H, d, J=8.0 Hz); 7.75 (1H, d, J=8.5 Hz); 8.07 (1H, d, J=7.5 Hz); 10.88 (1H, bs, NH); 10.95 (1H, bs, NH)

$^{13}$C NMR (100 MHz, DMSO-d$_6$): 102.8; 111.2; 112.0; 112.1; 118.6; 119.0; 123.3; 123.6 (CH); 116.2; 121.8; 124.1; 126.2; 126.4; 138.1 (C)

Example 3

1,10-dihydropyrrolo[2,3-a]carbazole-3-carbaldehyde

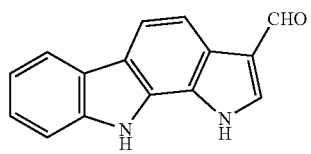 [SMILES: O=Cc1c[nH]c2c1ccc1c3ccccc3[nH]c12]

A solution of oxalyl chloride (19.5 µL; 0.223 mmol) and of DMF (18.9 µL; 0.244 mmol) in anhydrous dichloromethane (6 mL) is stirred at 0° C. for 20 minutes. A solution of the compound of Example 2 (43.6 mg; 0.211 mmol) in anhydrous dichloromethane (6 mL) is then added dropwise. The mixture is stirred at 0° C. for 20 minutes and then for 2.5 hours at room temperature. The solvent is evaporated off and aqueous 5% m/v NaOH solution (12 mL) is then added. The mixture is stirred at room temperature for 12 hours and water is then added. After extracting with EtOAc, the organic phase is dried over MgSO$_4$, filtered and evaporated. The residue is purified by chromatography on flash silica gel (elution gradient from 7/3 to 5/5 cyclohexane/EtOAc) to give the expected compound (32.4 mg; 0.138 mmol; yield=66%) in the form of an off-white solid.

Melting point >290° C.

IR (KBr): 3450-3150, 1630, 1615 cm$^{-1}$

High resolution mass spectrum (ESI+): calculated for $C_{15}H_{11}N_2O$ (M+H)$^+$ 235.0871. found 235.0882.

$^1$H NMR (500 MHz, DMSO-d$_6$): 7.23 (1H, t, J=7.5 Hz); 7.40 (1H, t, J=7.5 Hz); 7.70 (1H, d, J=8.0 Hz); 7.96 (1H, d, J=8.5 Hz); 8.00 (1H, d, J=8.5 Hz); 8.15 (1H, d, J=7.5 Hz); 8.33 (1H, d, J=2.0 Hz); 10.07 (1H, s); 11.10 (1H, bs); 11.93 (1H, bs)

$^{13}$C NMR (125 MHz, DMSO-d$_6$): 111.5; 112.1; 115.0; 119.0; 119.5; 124.3; 136.7 (CH); 118.3; 119.5; 122.5; 122.8; 123.5; 126.0; 138.5 (C); 185.3 (C=O)

Example 4

(1,10-dihydropyrrolo[2,3-a]carbazol-3-yl)methanol

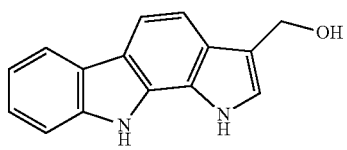 [SMILES: OCc1c[nH]c2c1ccc1c3ccccc3[nH]c12]

NaBH$_4$ (320 mg; 8.46 mmol) is added to a solution of the compound of Example 3 (147 mg; 0.63 mmol) in methanol (30 mL) and the mixture is stirred at room temperature for 1 hour. Water (10 mL) is added and the precipitate is recovered by filtration. The solid obtained is washed with methanol (5 mL) and then with Et$_2$O (2×20 mL) to give the expected compound (100 mg; 0.423 mmol; yield=67%) in the form of a gray solid.

Melting point >295° C.

IR (KBr): 3375, 1648, 1456 cm$^{-1}$

High resolution mass spectrum (ESI+): calculated for $C_{15}H_{11}N_2$ (M−OH)$^+$ 219.0922. found 219.0922.

$^1$H NMR (400 MHz, DMSO-d$_6$): 4.72 (2H, s); 4.54-4.96 (1H, bs); 7.14 (1H, t, J=7.5 Hz); 7.26-7.31 (2H, m); 7.40 (1H, d, J=8.5 Hz); 7.58 (1H, d, J=8.0 Hz); 7.71 (1H, d, J=8.5 Hz); 8.03 (1H, d, J=7.5 Hz); 10.48-11.46 (2H, 2 bs)

$^{13}$C NMR (100 MHz, DMSO-d$_6$): 55.7 (CH$_2$); 110.9; 111.1; 111.5; 118.5; 119.0; 121.8; 123.3 (CH); 116.3; 117.7; 122.1; 124.1; 125.1; 126.4; 138.1 (C)

Example 5

1,10-dihydropyrrolo[2,3-a]carbazole-3-carboxamide

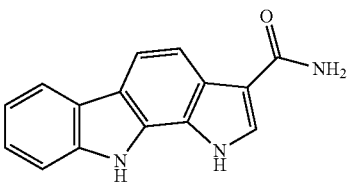 [SMILES: NC(=O)c1c[nH]c2c1ccc1c3ccccc3[nH]c12]

Chlorosulfonyl isocyanate (26.7 µL; 0.307 mmol) is added at 0° C. to a solution of the compound of Example 2 (57.4 mg; 0.278 mmol) in anhydrous acetonitrile (10 mL). The mixture is stirred at 0° C. for 1.5 hours, and an aqueous 1N HCl solution (5 mL) and THF (2 mL) are then added. The mixture is stirred at room temperature for 36 hours, and water is then added. After extracting with ethyl acetate, the combined organic phases are washed with saturated aqueous NaHCO$_3$ solution and with saturated aqueous NaCl solution, and then dried over MgSO$_4$, filtered and evaporated. The residue is purified by chromatography on flash silica gel (THF) to give the expected product (13.8 mg; 0.055 mmol; yield=20%) in the form of a beige-colored solid.

Melting point >300° C.

IR (KBr): 3430, 3370, 3335, 1650 cm$^{-1}$

High resolution mass spectrum (ESI+): calculated for $C_{15}H_{12}N_3O$ (M+H)$^+$ 250.0980. found 250.0966.

$^1$H NMR (500 MHz, DMSO-d$_6$): 6.86 (1H, bs); 7.20 (1H, t, J=8.0 Hz); 7.36 (1H, ddd, J$_1$=8.0 Hz, J$_2$=7.0 Hz, J$_3$=1.0 Hz); 7.46 (1H, bs); 7.65 (1H, d, J=8.0 Hz); 7.84 (1H, d, J=8.5 Hz); 8.02 (1H, d, J=8.5 Hz); 8.08 (1H, d, J=3.0 Hz); 8.10 (1H, d, J=8.0 Hz)

$^{13}$C NMR (100 MHz, DMSO-d$_6$): 111.3; 112.8; 113.2; 118.7; 119.2; 123.7; 126.8 (CH); 112.1; 116.8; 112.1; 123.8; 124.8; 126.2; 138.3 (C); 166.7 (C=O)

Example 6

1-(1,10-dihydropyrrolo[2,3-a]carbazol-3-yl)-2,2,2-trifluoroethanone

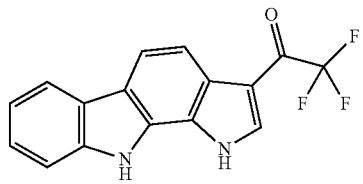 [SMILES: O=C(c1c[nH]c2c1ccc1c3ccccc3[nH]c12)C(F)(F)F]

Trifluoroacetic anhydride (45 μL; 0.32 mmol) is added at room temperature to a solution of the compound of Example 2 (52 mg; 0.25 mmol) in DMF (10 mL). The mixture is stirred at room temperature for 18 hours, and ice and water are then added. The mixture is extracted with ethyl acetate (3×10 mL) and the combined organic fractions are then washed with saturated aqueous NaCl solution (15 mL), dried over MgSO$_4$, filtered and evaporated. The residue obtained is triturated with Et$_2$O (20 mL) and the mixture is filtered, to give the expected compound (32 mg; 0.106 mmol; yield=42%) in the form of a green solid.

Melting point >295° C.

IR (KBr): 3274, 1639 cm$^{-1}$

High resolution mass spectrum (ESI+): calculated for $C_{16}H_{10}F_3N_2O$ (M+H)$^+$ 303.0745. found 303.0732.

$^1$H NMR (400 MHz, DMSO-d$_6$): 7.22 (1H, t, J=7.5 Hz); 7.40 (1H, ddd, J$_1$=8.0 Hz, J$_2$=7.0 Hz, J$_3$=1.0 Hz); 7.70 (1H, d, J=8.0 Hz); 8.01 (1H, d, J=8.5 Hz); 8.07 (1H, d, J=8.5 Hz); 8.15 (1H, d, J=8.0 Hz); 8.49-8.53 (1H, bs); 11.03 (1H, s); 12.39-12.48 (1H, bs)

$^{13}$C NMR (100 MHz, DMSO-d$_6$): 111.7; 112.1; 116.3; 119.3; 119.7; 124.7; 135.8 (q, J$_{CF}$=5 Hz) (CH); 110.1; 117.0 (q, J$_{CF}$=292 Hz); 119.1; 122.3; 123.2; 124.1; 126.0; 138.6 (C); 174.0 (q, J$_{CF}$=34 Hz, C=O)

Example 7 methyl 2-(1,10-dihydropyrrolo[2,3-a]carbazol-3-yl)-2-oxoacetate

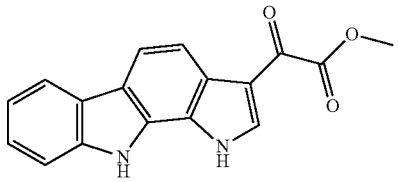 [SMILES: COC(=O)C(=O)c1c[nH]c2c1ccc1c3ccccc3[nH]c12]

Stage A:

oxalyl chloride (660 μL; 7.7 mmol) is added at 0° C. to a suspension of the compound of Example 2 (825 mg; 4.00 mmol) in anhydrous Et$_2$O (40 mL). The mixture is stirred at room temperature for 4 hours. After filtration, the solid is washed with Et$_2$O (2×40 mL) to give the intermediate acid chloride (972 mg) in the form of a red-brown solid, which is used without further purification.

Stage B:

Et$_3$N (138 μL; 0.99 mmol) is added to a suspension of the intermediate acid chloride (243 mg) in methanol (5 mL). The mixture is stirred at room temperature for 4 hours. After filtration, the solid is washed with MeOH (5 mL) and then with Et$_2$O (2×20 mL) to give the expected compound (176 mg; 0.60 mmol; yield=60% from the compound of Example 2) in the form of a dark orange solid.

Melting point >290° C.

IR (KBr): 3461, 3306, 1735, 1590 cm$^{-1}$

High resolution mass spectrum (ESI+): calculated for $C_{17}H_{12}N_2NaO_3$ (M+Na)$^+$ 315.0746. found 315.0754.

$^1$H NMR (400 MHz, DMSO-d$_6$): 3.92 (3H, 5); 7.20 (1H, ddd, J$_1$=8.0 Hz, J$_2$=7.0 Hz, J$_3$=1.0 Hz); 7.38 (1H, ddd, J$_1$=8.0 Hz, J$_2$=7.0 Hz, J$_3$=1.0 Hz); 7.67 (1H, d, J=8.0 Hz); 7.99 (1H, d, J=8.5 Hz); 8.02 (1H, d, J=8.5 Hz); 8.13 (1H, d, J=8.0 Hz); 8.49 (1H, d, J=3.5 Hz); 11.05 (1H, s, NH); 12.14-12.21 (1H, bs)

$^{13}$C NMR (100 MHz, DMSO-d$_6$): 52.5 (CH$_3$); 111.6; 112.3; 115.7; 119.1; 119.6; 124.5; 136.7 (CH); 113.7; 118.7; 122.4; 123.3; 123.8; 126.1; 138.5 (C); 164.1; 178.9 (C=O)

Example 8 ethyl 2-(1,10-dihydropyrrolo[2,3-a]carbazol-3-yl)-2-oxoacetate

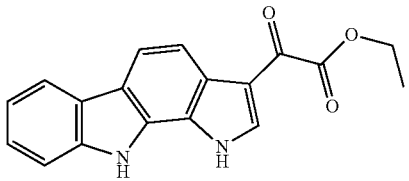 [SMILES: CCOC(=O)C(=O)c1c[nH]c2c1ccc1c3ccccc3[nH]c12]

Et$_3$N (275 μL; 1.97 mmol) is added to a suspension of the compound prepared in stage A and of Example 7 (486 mg) in ethanol (10 mL). The mixture is stirred at room temperature for 4 hours. After filtration, the solid is washed with EtOH (10 mL) and then with Et$_2$O (2×20 mL) to give the expected compound (446 mg; 1.46 mmol; yield=73% from the compound of Example 2) in the form of a green-yellow solid.

Melting point >295° C.

IR (KBr): 3292, 1725, 1602 cm$^{-1}$

High resolution mass spectrum (ESI+): calculated for $C_{18}H_{14}N_2NaO_3$ (M+Na)$^+$ 329.0902. found 329.0907.

$^1$H NMR (400 MHz, DMSO-d$_6$): 1.37 (3H, t, J=7.0 Hz); 4.39 (2H, q, J=7.0 Hz); 7.20 (1H, t, J=7.5 Hz); 7.38 (1H, ddd, J$_1$=8.0 Hz, J$_2$=7.0 Hz, J$_3$=1.0 Hz); 7.67 (1H, d, J=8.0 Hz); 7.98-8.03 (2H, m); 8.12 (1H, d, J=8.0 Hz); 8.47 (1H, d, J=3.0 Hz); 11.07 (1H, s); 12.09-12.20 (1H, bs)

$^{13}$C NMR (100 MHz, DMSO-d$_6$): 14.0 (CH$_3$); 61.6 (CH$_2$); 111.6; 112.3; 115.7; 119.1; 119.6; 124.5; 136.6 (CH); 113.7; 118.7; 122.4; 123.3; 123.8; 126.1; 138.5 (C); 163.7; 179.4 (C=O)

Example 9

2-(1,10-dihydropyrrolo[2,3-a]carbazol-3-yl)ethanol

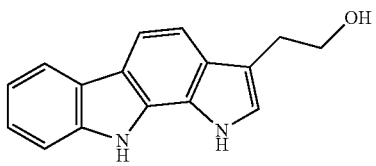 [SMILES: OCCc1c[nH]c2c1ccc1c3ccccc3[nH]c12]

LiAlH$_4$ (2.00 mL; 2.00 mmol; 1M in THF) is added at room temperature to a suspension of the compound of Example 8 (153 mg; 0.50 mmol) in dioxane (10 mL). The THF is distilled off and the mixture is then refluxed for 12 hours. After cooling to room temperature, water (5 mL) is added and the mixture is extracted with EtOAc (3×10 mL). The combined organic fractions are washed with water (10 mL), dried over MgSO$_4$, filtered and evaporated. The residue is triturated in Et$_2$O (20 mL) and then filtered, to give the expected compound (90 mg; 0.36 mmol; yield=72%) in the form of a gray-brown solid.

Melting point: 269-271° C.
IR (KBr): 3416, 3382, 3234, 1649, 1457 cm$^{-1}$
High resolution mass spectrum (ESI+): calculated for C$_{16}$H$_{15}$N$_2$O (M+H)$^+$251.1184. found 251.1177.
$^1$H NMR (400 MHz, DMSO-d$_6$): 2.92 (2H, t, J=7.5 Hz); 3.71 (2H, dt, J$_1$=7.5 Hz, J$_2$=5.5 Hz); 4.63 (1H, t, J=5.5 Hz); 7.13 (1H, ddd, J$_1$=8.0 Hz, J$_2$=7.0 Hz, J$_3$=1.0 Hz); 7.19 (1H, d, J=2.0 Hz); 7.28 (1H, ddd, J$_1$=8.0, J$_2$=7.0 Hz, J$_3$=1.0 Hz); 7.31 (1H, d, J=8.5 Hz); 7.58 (1H, d, J=8.0 Hz); 7.70 (1H, d, J=8.5 Hz); 8.02 (1H, d, J=7.5 Hz); 10.53-10.57 (1H, bs); 10.86 (1H, s)
$^{13}$C NMR (100 MHz, DMSO-d$_6$): 29.1; 61.8 (CH$_2$); 110.4; 111.1; 111.3; 118.5; 119.0; 121.2; 123.2 (CH); 113.3; 116.2; 121.9; 124.1; 125.9; 126.5; 138.1 (C)

Example 10

2-(1,10-dihydropyrrolo[2,3-a]carbazol-3-yl)-N,N-diethyl-2-oxoacetamide

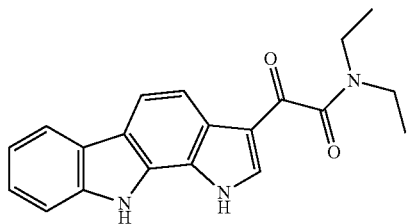 [SMILES: CCN(CC)C(=O)C(=O)c1c[nH]c2c1ccc1c3ccccc3[nH]c12]

Diethylamine (305 µL; 2.92 mmol) is added to a suspension of the compound prepared in stage A of Example 7 (486 mg) in anhydrous Et$_2$O (10 mL). The mixture is stirred at room temperature for 4 hours. After filtration, the solid is washed with MeOH (3 mL) and then with Et$_2$O (2×20 mL) to give the expected compound (439 mg; 1.32 mmol; yield=66% from the compound of Example 2) in the form of a pale gray solid.

Melting point >295° C.
IR (KBr): 3450-3100, 1608, 1429 cm$^{-1}$
High resolution mass spectrum (ESI+): calculated for C$_{20}$H$_{20}$N$_3$O$_2$ (M+H)$^+$334.1556. found 334.1543.
$^1$H NMR (400 MHz, DMSO-d$_6$): 1.10 (3H, t, J=7.0 Hz); 1.22 (3H, t, J=7.0 Hz); 3.28 (2H, q, J=7.0 Hz); 3.47 (2H, q, J=7.0 Hz); 7.20 (1H, ddd, J$_1$=8.0 Hz, J$_2$=7.0 Hz, J$_3$=1.0 Hz); 7.37 (1H, ddd, J$_1$=8.0 Hz, J$_2$=7.0 Hz, J$_3$=1.5 Hz); 7.66 (1H, d, J=8.0 Hz); 7.93 (1H, d, J=8.5 Hz); 7.99 (1H, d, J=8.5 Hz); 8.07 (1H, d, J=3.0 Hz); 8.12 (1H, d, J=8.0 Hz); 11.04 (1H, s, NH); 11.96-12.01 (1H, bs, NH)
$^{13}$C NMR (100 MHz, DMSO-d$_6$): 12.7; 14.1 (CH$_3$); 38.1; 41.7 (CH$_2$); 111.4; 112.1; 115.3; 119.0; 119.5; 124.4; 134.9 (CH); 114.3; 118.3; 122.7; 123.2; 123.4; 126.1; 138.4 (C); 167.2; 187.0 (C=O)

Example 11

2-(1,10-dihydropyrrolo[2,3-a]carbazol-3-yl)-N,N-diethylethanamine

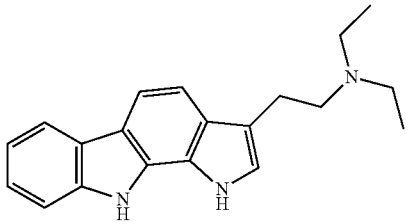 [SMILES: CCN(CC)CCc1c[nH]c2c1ccc1c3ccccc3[nH]c12]

LiAlH$_4$ (2.00 mL; 2.00 mmol; 1 M in THF) is added under argon at room temperature to a suspension of the compound of Example 10 (120 mg; 0.360 mmol) in dioxane (10 mL). The THF is distilled off and the mixture is then refluxed for 12 hours. After cooling to room temperature, a drop of water is added and the mixture is filtered. The filtrate is concentrated and the residue is then triturated with Et$_2$O (20 mL). After filtration, the solid is washed with Et$_2$O (20 mL) to give the expected compound (27 mg; 0.088 mol; yield=25%) in the form of a gray solid.

Melting point: 224-226° C.
IR (KBr): 3388, 1649, 1560, 1450 cm$^{-1}$
High resolution mass spectrum (ESI+): calculated for C$_{20}$H$_{24}$N$_3$ (M+H)$^+$306.1970. found 306.1960.
$^1$H NMR (400 MHz, DMSO-d$_6$): 1.02 (6H, t, J=7.0 Hz); 2.59 (4H, q, J=7.0 Hz); 2.71-2.76 (2H, m); 2.83-2.89 (2H, m); 7.13 (1H, ddd, J$_1$=8.0 Hz, J$_2$=7.0 Hz, J$_3$=1.0 Hz); 7.18-7.20 (1H, m); 7.26-7.31 (2H, m); 7.58 (1H, d, J=8.0 Hz); 7.70 (1H, d, J=8.5 Hz); 8.02 (1H, d, J=7.5 Hz); 10.52-10.56 (1H, bs); 10.86 (1H, s)
$^{13}$C NMR (100 MHz, DMSO-d$_6$): 12.0 (CH$_3$); 22.8; 46.3 (2C); 53.4 (CH$_2$); 110.2; 111.1; 111.3; 118.5; 118.9; 120.9; 123.2 (CH); 114.7; 116.2; 121.9; 124.0; 125.8; 126.5; 138.1 (C)

Example 12

1-(1,10-dihydropyrrolo[2,3-a]carbazol-3-yl)-2-diethylaminoethanol

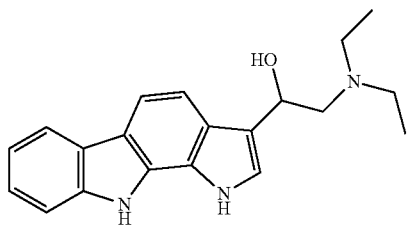 [SMILES: CCN(CC)CC(O)c1c[nH]c2c1ccc1c3ccccc3[nH]c12]

LiAlH$_4$ (2.00 mL; 2.00 mmol; 1M in THF) is added to a suspension of the compound of Example 10 (181 mg; 0.543 mmol) in THF (10 mL) and the mixture is stirred at reflux for 24 hours. Water (76 µL), aqueous 15% NaOH solution (76 µL) and then water (228 µL) are successively added. The mixture is filtered and the filtrate is concentrated. The residue obtained is washed with water (3 mL), dried, washed with MeOH (3 mL) and then finally with Et$_2$O (10 mL) to give the expected compound (57 mg; 0.177 mmol; yield=33%) in the form of an off-white solid.

Melting point: 148-150° C.
IR (KBr): 3274, 1652, 1615, 1455 cm$^{-1}$
High resolution mass spectrum (ESI+): calculated for C$_{20}$H$_{24}$N$_3$O (M+H)$^+$322.1919. found 322.1912.
$^1$H NMR (400 MHz, DMSO-d$_6$): 0.99 (6H, t, J=7.0 Hz); 2.53-2.69 (4H, m); 2.74 (1H, dd, J$_1$=13.0 Hz, J$_2$=5.0 Hz); 2.78 (1H, dd, J$_1$=13.0 Hz, J$_2$=7.5 Hz); 4.55-4.63 (1H, bs); 4.98 (1H, dd, J$_1$=7.5 Hz, J$_2$=5.0 Hz); 7.13 (1H, t, J=7.5 Hz); 7.26-7.31 (2H, m); 7.41 (1H, d, J=8.5 Hz); 7.58 (1H, d, J=8.0 Hz); 7.69 (1H, d, J=8.5 Hz); 8.02 (1H, d, J=7.5 Hz); 10.60-10.65 (1H, bs); 10.87 (1H, s)
$^{13}$C NMR (100 MHz, DMSO-d$_6$): 11.9 (CH$_3$); 46.8 (2C); 60.3 (CH$_2$); 65.0; 111.1; 111.3; 111.4; 118.5; 119.0; 120.7; 123.3 (CH); 116.1; 119.6; 122.2; 124.0; 124.4; 126.4; 138.1 (C)

Example 13

2-(1,10-dihydropyrrolo[2,3-a]carbazol-3-yl)-N,N-diethyl-2-hydroxyiminoethanamide

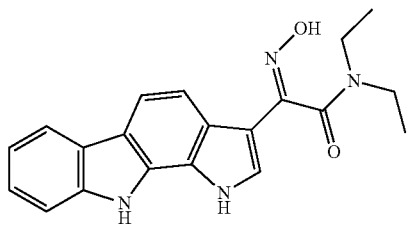 [SMILES: CCN(CC)C(=O)/C(=N\O)c1c[nH]c2c1ccc1c3ccccc3[nH]c12]

Hydroxylamine hydrochloride (261 mg; 3.76 mmol) is added to a solution of the compound of Example 10 (167 mg; 0.50 mmol) in pyridine (5 mL) and the mixture is then refluxed for 12 hours. Water (5 mL) is added and the pyridine is evaporated off under reduced pressure. The mixture is extracted with ethyl acetate (3×10 mL) and the combined organic fractions are washed with saturated aqueous NaCl solution (10 mL), dried over MgSO$_4$, filtered and evaporated. The residue obtained is triturated with EtOAc (20 mL) and the mixture is filtered, to give the expected compound (33 mg; 0.095 mmol; yield=19%) in the form of a beige-colored solid.

Melting point: 268-269° C.
IR (KBr): 3266, 1609, 1464 cm$^{-1}$
High resolution mass spectrum (ESI+): calculated for C$_{20}$H$_{21}$N$_4$O$_2$ (M+H)$^+$349.1665. found 349.1675.
$^1$H NMR (400 MHz, DMSO-d$_6$): 1.03 (3H, t, J=7.0 Hz); 1.19 (3H, t, J=7.0 Hz); 3.26 (2H, q, J=7.0 Hz); 3.39-3.59 (2H, m); 7.17 (1H, t, J=7.5 Hz); 7.33 (1H, t, J=7.5 Hz); 7.36 (1H, d, J=2.5 Hz); 7.61 (1H, d, J=8.0 Hz); 7.83 (1H, d, J=8.5 Hz); 7.86 (1H, d, J=8.5 Hz); 8.07 (1H, d, J=7.5 Hz); 10.90 (1H, s); 11.03-11.07 (1H, bs); 11.21-11.26 (1H, bs)
$^{13}$C NMR (100 MHz, DMSO-d$_6$): 12.8; 13.8 (CH$_3$); 37.6; 41.7 (CH$_2$); 111.3; 113.2; 113.3; 118.7; 119.3; 123.8; 125.7 (CH); 109.7; 117.3; 122.5; 122.7; 123.7; 126.2; 138.3 (C); 150.6 (C=N); 164.4 (C=O)

Example 14

1-benzenesulfonyl-7-bromo-1,10-dihydropyrrolo-[2,3-a]carbazole

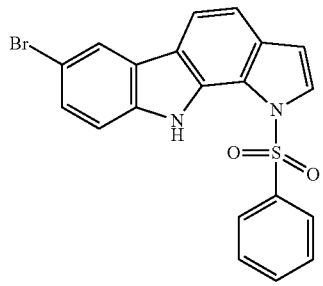 [SMILES: O=S(=O)(c1ccccc1)n1ccc2ccc3c4cc(Br)ccc4[nH]c3c21]

A suspension of 4-bromophenylhydrazine chloride (1.62 g; 7.3 mmol) and anhydrous sodium acetate (0.60 g; 7.3 mmol) in DME (20 mL) is stirred at room temperature for 1 hour. The compound of Preparation B (1.00 g; 3.63 mmol) and the ionic liquid of Preparation C (10.0 g; 24.3 mmol) are added. The solvent is evaporated off and the reaction mixture is stirred at 120° C. for 2 hours. The brown oil obtained is cooled and aqueous 0.5 M HCl solution is added. The mixture is extracted three times with ethyl acetate. The combined organic phases are washed with saturated aqueous NaCl solution, dried over MgSO$_4$, filtered and evaporated. The residue obtained is a mixture containing the indolization product, as the major product, and the expected product, as the minor product.

A solution of the residue obtained and of DDQ (0.7 g; 3.1 mmol; the required amount of DDQ is determined from the $^1$H NMR spectrum of the residue obtained) in dioxane (20 mL) is stirred at room temperature for 15 hours. After evaporating off the solvent, ethyl acetate is added and the mixture is washed with water and saturated aqueous NaCl solution. The organic solution is dried over MgSO$_4$, filtered and then concentrated on silica, followed by purification by chromatography on flash silica gel (9/1 pentane/ethyl acetate) to give the expected compound (1.15 g; 2.70 mmol; yield=74%) in the form of a brown solid.

Melting point: 173-175° C.
IR (KBr): 3434, 1631 cm$^{-1}$
High resolution mass spectrum (ESI+): calculated for C$_{20}$H$_{14}$$^{79}$BrN$_2$O$_2$S (M+H)$^+$ 424.9959. found 424.9976.

¹H NMR (400 MHz, DMSO-d₆): 7.04 (1H, d, J=3.5 Hz); 7.41 (1H, d, J=8.0 Hz); 7.49-7.55 (3H, m); 7.62 (1H, t, J=7.5 Hz); 7.84 (1H, d, J=3.5 Hz); 7.92-7.99 (3H, m); 8.12 (1H, d, J=8.0 Hz); 8.38 (1H, d, J=1.5 Hz); 10.81 (1H, s, NH).

¹³C NMR (100 MHz, DMSO-d₆): 112.4; 113.2; 114.9; 117.4; 121.9; 126.7 (2C); 127.0; 127.5; 129.9 (2C); 134.6 (CH); 111.7; 119.4; 120.1; 124.7; 126.6; 130.8; 136.8; 137.7 (C).

Example 15

7-bromo-1,10-dihydropyrrolo[2,3-a]carbazole

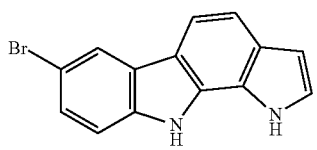 [SMILES: Brc1ccc2[nH]c3c(ccc4cc[nH]c43)c2c1]

Aqueous 5 N NaOH solution (10 mL) is added to a suspension of the compound of Example 14 (500 mg; 1.18 mmol) in methanol (100 mL). The mixture is refluxed for 12 hours. The reaction mixture is concentrated under vacuum until a precipitate forms. The mixture is neutralized with concentrated aqueous HCl solution and the solid is then collected by filtration and washed with water, to give the expected compound (310 mg; 1.09 mmol; yield=92%) in the form of a brown solid.

Melting point: 250° C. (decomposition)

High resolution mass spectrum (ESI+) calculated for $C_{14}H_{10}{}^{79}BrN_2$ (M+H)⁺285.0027. found 285.0040.

IR (KBr): 3400, 1648, 1438 cm⁻¹

¹H NMR (400 MHz, DMSO-d₆): 6.59 (1H, dd, J₁=3.0 Hz, J₂=2.0 Hz); 7.35 (1H, d, J=8.5 Hz); 7.38-7.42 (2H, m); 7.58 (1H, d, J=8.5 Hz); 7.74 (1H, d, J=8.5 Hz); 8.25 (1H, d, J=2.0 Hz); 10.88-10.92 (1H, bs, NH); 11.05-11.09 (1H, bs, NH)

¹³C NMR (100 MHz, DMSO-d₆): 102.9; 112.2; 112.6; 113.1; 121.5; 124.0; 125.6 (CH); 110.8; 115.3; 121.5; 126.1; 126.7; 127.1; 136.8 (C)

Example 16

7-bromo-1,10-dihydropyrrolo[2,3-a]carbazole-3-carbaldehyde

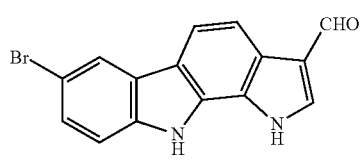 [SMILES: O=Cc1c[nH]c2c1ccc1c3cc(Br)ccc3[nH]c12]

A solution of oxalyl chloride (32.5 μL; 0.38 mmol) and of DMF (31.2 μL; 0.40 mmol) in anhydrous dichloromethane (10 mL) is stirred at 0° C. for 20 minutes. A solution of the compound of Example 15 (100 mg; 0.35 mmol) in anhydrous dichloromethane (10 mL) is added dropwise. The mixture is stirred at 0° C. for 20 minutes and then allowed to warm to room temperature. The solvent is evaporated off and aqueous 5% m/v NaOH solution (20 mL) is then added. The mixture is stirred at room temperature for 12 hours and then extracted with ethyl acetate. The organic phase is washed with water, with saturated aqueous NaCl solution, dried over MgSO₄, filtered and then evaporated. The residue is purified by chromatography on flash silica gel (7/3 and then 5/5 cyclohexane/EtOAc) to give the expected compound (72 mg; 0.230 mmol; yield=66%) in the form of a gray solid.

Melting point >250° C.

High resolution mass spectrum (ESI+) calculated for $C_{15}H_{10}{}^{79}BrN_2O$ (M+H)⁺312.9976. found 312.9979.

IR (KBr): 3400-3100, 1630 cm⁻¹

¹H NMR (400 MHz, DMSO-d₆): 7.48 (1H, dd, J₁=8.5 Hz, J₂=2.0 Hz); 7.65 (1H, d, J=8.5 Hz); 7.94 (1H, d, J=8.5 Hz); 8.00 (1H, d, J=8.5 Hz); 8.31 (1H, d, J=3.0 Hz); 8.34 (1H, d, J=2.0 Hz); 10.04 (1H, s); 11.18-11.23 (1H, bs, NH); 11.89-11.96 (1H, bs, NH)

¹³C NMR (100 MHz, DMSO-d₆): 112.6; 113.5; 115.3; 122.0; 126.6; 137.0 (CH); 111.2; 117.4; 119.5; 122.5; 123.1; 125.5; 126.6; 137.2 (C); 185.4 (C=O)

General Procedure for Preparing the Compounds of Examples 17-19

To a solution of the compound of Example 14 (425 mg; 1 mmol) in THF (5 mL) are added a solution of sodium carbonate (212 mg; 2 equivalents) in water (1 mL), Pd(PPh₃)₂Cl₂ (35.1 mg; 5 mol %) and the corresponding boric acid (1.1 equivalents). The reaction mixture is refluxed overnight under argon. After cooling to room temperature, the mixture is filtered through Celite and the solid is washed with acetone. After evaporation, methanol (40 mL) and aqueous 5 M NaOH solution (20 mL) are added to the residue obtained, and the mixture is refluxed for 12 hours. The reaction mixture is concentrated under vacuum and then neutralized with concentrated aqueous HCl solution. Ethyl acetate is added, the organic phase is collected, and the aqueous phase is extracted with ethyl acetate (3×30 mL). The combined organic phases are washed with saturated aqueous NaCl solution, dried over MgSO₄, filtered and evaporated. The residue is purified by chromatography on flash silica gel (9/1, 8/2 and then 7/3 pentane/ethyl acetate) to give the expected compound.

Example 17

7-(4-acetylphenyl)-1,10-dihydropyrrolo[2,3-a]carbazole

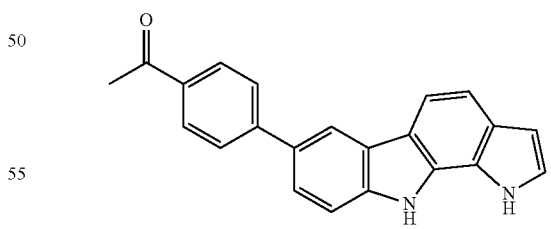

The expected compound (195 mg; 0.60 mmol; yield=60%) is obtained in the form of a brown solid.

Melting point: 185° C. (decomposition)

High resolution mass spectrum (ESI+): calculated for $C_{22}H_{17}N_2O$ (M+H)⁺325.1341. found 325.1354.

IR (KBr): 3700-3100, 1649, 1597 cm⁻¹

¹H NMR (400 MHz, DMSO-d₆): 2.63 (3H, s, CH₃); 6.59-6.61 (1H, m); 7.38 (1H, d, J=8.5 Hz); 7.39-7.41 (1H, m); 7.71-7.73 (2H, m); 7.84 (1H, d, J=8.5 Hz); 7.96 (2H, d, J=8.5

Hz); 8.06 (2H, d, J=8.5 Hz); 8.48 (1H, s); 10.86-10.90 (1H, bs, NH); 11.05-11.08 (1H, bs, NH)

$^{13}$C NMR (100 MHz, DMSO-d$_6$): 26.7 (CH$_3$); 102.9; 111.8; 112.2; 112.5; 117.7; 122.6; 123.9; 126.5 (2C); 128.9 (2C) (CH); 116.3; 121.7; 124.9; 126.6; 127.0; 129.6; 134.5; 138.3; 146.1 (C); 197.4 (C=O)

Example 18

7-(3-methoxyphenyl)-1,10-dihydropyrrolo[2,3-a]-carbazole

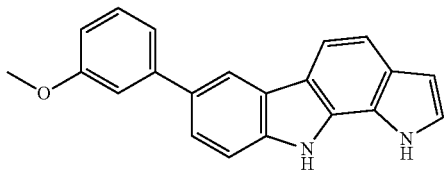 [SMILES: COc1cccc(-c2ccc3[nH]c4c(ccc5cc[nH]c54)c3c2)c1]

The expected compound (172 mg; 0.55 mmol; yield=55%) is obtained in the form of a brown solid.

Melting point: 202-205° C.

High resolution mass spectrum (ESI+) calculated for C$_{21}$H$_{17}$N$_2$O (M+H)$^+$313.1341. found 313.1343.

IR (KBr): 3390, 1654, 1609, 1584, 1461 cm$^{-1}$ $^1$H NMR (400 MHz, DMSO-d$_6$): 3.86 (3H, s, CH$_3$); 6.59 (1H, dd, J$_1$=3.0 Hz, J$_2$=2.0 Hz); 6.90 (1H, ddd, J$_1$=8.0 Hz, J$_2$=2.5 Hz, J$_3$=1.5 Hz); 7.29-7.31 (1H, m); 7.34 (1H, dt, J$_1$=7.5 Hz, J$_2$=1.5 Hz); 7.36 (1H, d, J=8.5 Hz); 7.39 (1H, t, J=7.5 Hz); 7.39 (1H, t, J=2.5 Hz); 7.61 (1H, dd, J$_1$=8.5 Hz, J$_2$=1.5 Hz); 7.67 (1H, d, J=8.5 Hz); 7.82 (1H, d, J=8.5 Hz); 8.36 (1H, d, J=1.5 Hz); 10.83-10.88 (1H, bs, NH); 10.95-11.0 (1H, bs, NH)

$^{13}$C NMR (100 MHz, DMSO-d$_6$): 55.1 (CH$_3$); 102.8; 111.5; 111.8; 112.2 (3C); 117.3; 119.1; 122.6; 123.7; 129.8 (CH); 116.4; 121.8; 124.7; 126.4; 127.0; 131.0; 137.8; 143.2; 159.7 (C)

Example 19

7-(4-biphenyl)-1,10-dihydropyrrolo[2,3-a]carbazole

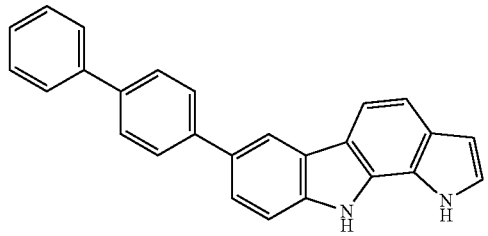 [SMILES: c1ccc(-c2ccc(-c3ccc4[nH]c5c(ccc6cc[nH]c65)c4c3)cc2)cc1]

The expected compound (230 mg; 0.64 mmol; yield=64%) is obtained in the form of a brown solid.

Melting point >250° C.

High resolution mass spectrum (ESI+): calculated for C$_{26}$H$_{18}$N$_2$ (M)$^+$358.1470. found 358.1492.

IR (KBr): 3650-3100, 1698, 1648 cm$^{-1}$ $^1$H NMR (400 MHz, DMSO-d$_6$): 6.60 (1H, dd, J$_1$=3.0 Hz, J$_2$=2.0 Hz); 7.36-7.41 (3H, m); 7.47-7.52 (2H, m); 7.68 (1H, dd, J$_1$=8.5 Hz, J$_2$=1.5 Hz); 7.71 (1H, dd, J$_1$=8.5 Hz, J$_2$=0.5 Hz); 7.73-7.76 (2H, m); 7.77-7.80 (2H, m); 7.83 (1H, d, J=8.5 Hz); 7.87-7.91 (2H, m); 8.41-8.43 (1H, m); 10.83-10.89 (1H, bs, NH); 10.98-11.02 (1H, bs, NH)

$^{13}$C NMR (100 MHz, DMSO-d$_6$): 102.8; 111.6; 112.2; 112.3; 117.1; 122.4; 123.7; 126.4 (2C); 127.0 (2C); 127.1 (2C); 127.3; 128.9 (2C) (CH); 116.4; 121.8; 124.8; 126.5; 127.0; 130.4; 137.8; 137.9; 139.8; 140.6 (C)

Example 20

7-phenyl-1,10-dihydropyrrolo[2,3-a]carbazole

The expected compound (169 mg; 0.60 mmol; yield=60%) is obtained in the form of a gray solid.

Melting point >250° C.

High resolution mass spectrum (ESI+) calculated for C$_{20}$H$_{15}$N$_2$ (M+H)$^+$283.1235. found 283.1248.

IR (KBr): 3434, 3368, 1652 cm$^{-1}$ $^1$H NMR (400 MHz, DMSO-d$_6$): 6.59 (1H, dd, J$_1$=3.0 Hz, J$_2$=2.0 Hz); 7.30-7.35 (1H, m); 7.37 (1H, J$_1$=8.5 Hz, J$_2$=0.5 Hz); 7.40 (1H, dd, J$_1$=3.0 Hz, J$_2$=2.5 Hz); 7.45-7.50 (2H, m); 7.61 (1H, dd, J$_1$=8.5 Hz, J$_2$=2.0 Hz); 7.68 (1H, dd, J$_1$=8.5 Hz, J$_2$=0.5 Hz); 7.76-7.79 (2H, m); 7.82 (1H, dd, J$_1$=8.5 Hz, J$_2$=0.5 Hz); 8.35 (1H, d, J=2.0 Hz); 10.83-10.89 (1H, bs, NH); 10.96-11.00 (1H, bs, NH)

$^{13}$C NMR (100 MHz, DMSO-d$_6$): 102.9; 111.6; 112.2; 112.3; 117.2; 122.5; 123.7; 126.2; 126.7 (2C); 128.8 (2C) (CH); 116.4; 121.8; 124.8; 126.4; 127.0; 131.1; 137.8; 141.6 (C)

Example 21

7-(4-fluorophenyl)-1,10-dihydropyrrolo[2,3-a]carbazole

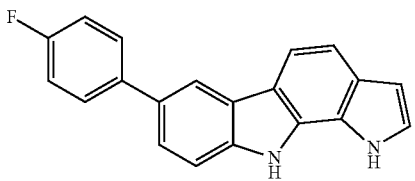 [SMILES: Fc1ccc(-c2ccc3[nH]c4c(ccc5cc[nH]c54)c3c2)cc1]

The expected compound (150 mg; 0.50 mmol; yield=50%) is obtained in the form of a gray-green solid.

Melting point >250° C.

High resolution mass spectrum (ESI+) calculated for C$_{20}$H$_{14}$FN$_2$ (M+H)$^+$301.1141. found 301.1154.

IR (KBr): 3410, 3397, 1651, 1605, 1514 cm$^{-1}$ $^1$H NMR (400 MHz, DMSO-d$_6$): 6.59 (1H, dd, J$_1$=3.0 Hz, J$_2$=2.0 Hz); 7.27-7.33 (2H, m); 7.36 (1H, d, J=8.5 Hz); 7.39 (1H, dd, J$_1$=3.0 Hz, J$_2$=2.5 Hz); 7.58 (1H, dd, J$_1$=8.5 Hz, J$_2$=2.0 Hz); 7.68 (1H, dd, J$_1$=8.5 Hz, J$_2$=0.5 Hz); 7.77-7.83 (3H, m); 8.33 (1H, d, J=2.0 Hz); 10.84-10.87 (1H, bs, NH); 10.96-10.98 (1H, bs, NH)

$^{13}$C NMR (100 MHz, DMSO-d$_6$): 102.8; 111.6; 112.2; 112.3; 115.5 (2C, d, J$_{CF}$=21 Hz); 117.2; 122.4; 123.8; 128.5 (2C, d, J$_{CF}$=8 Hz) (CH); 116.3; 121.8; 124.8; 126.5; 127.0; 130.1; 137.7; 138.1 (d, J$_{CF}$=3 Hz); 161.2 (d, J$_{CF}$=243 Hz) (C)

Example 22

7-(2,4-difluorophenyl)-1,10-dihydropyrrolo[2,3-a]-carbazole

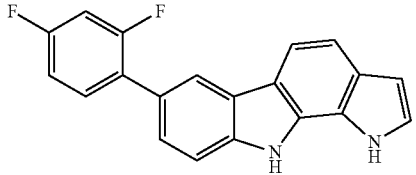 [SMILES: Fc1ccc(-c2ccc3[nH]c4c(ccc5cc[nH]c54)c3c2)c(F)c1]

The expected compound (165 mg; 0.52 mmol; yield=52%) is obtained in the form of a gray-green solid.

Melting point >250° C.

High resolution mass spectrum (ESI+) calculated for C$_{20}$H$_{13}$F$_2$N$_2$ (M+H)$^+$319.1047. found 319.1058.

IR (KBr): 3401, 1652, 1616, 1594, 1510 cm$^{-1}$ $^1$H NMR (400 MHz, DMSO-d$_6$): 6.59 (1H, dd, J$_1$=3.0 Hz, J$_2$=2.0 Hz); 7.21 (1H, tdd, J$_1$=8.5 Hz, J$_2$=3.0 Hz, J$_3$=1.0 Hz); 7.33-7.39 (2H, m); 7.40 (1H, t, J=2.5 Hz); 7.45 (1H, dt, J$_1$=8.5 Hz, J$_2$=2.0 Hz); 7.67 (1H, td, J$_1$=9.0 Hz, J$_2$=6.5 Hz); 7.69 (1H, d, J=8.5 Hz); 7.78 (1H, d, J=8.5 Hz); 8.19 (1H, s); 10.85-10.88 (1H, bs, NH); 11.03-11.06 (1H, bs, NH)

$^{13}$C NMR (100 MHz, DMSO-d$_6$): 102.9; 104.3 (dd, J$_{CF1}$=27 Hz, J$_{CF2}$=26 Hz); 111.3; 111.8 (dd, J$_{CF1}$=21 Hz, J$_{CF2}$=4 Hz); 112.1; 112.4; 119.4 (d, J$_{CF}$=3 Hz); 123.8; 124.3 (d, J$_{CF}$=3 Hz); 132.1 (dd, J$_{CF1}$=10 Hz, J$_{CF2}$=5 Hz) (CH); 116.2; 121.7; 124.4; 124.8 (d, J$_{CF}$=1 Hz); 126.3 (dd, J$_{CF1}$=14 Hz, J$_{CF2}$=4 Hz); 126.5; 126.9; 137.7; 159.1 (dd, J$_{CF1}$=247 Hz, J$_{CF2}$=12 Hz); 161.1 (dd, J$_{CF1}$=246 Hz, J$_{CF2}$=12 Hz)

Example 23

7-(4-trifluoromethylphenyl)-1,10-dihydropyrrolo-[2,3-a]carbazole

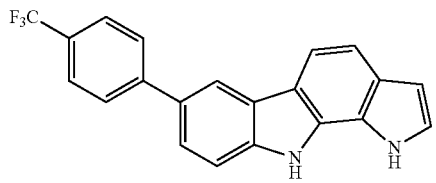 [SMILES: FC(F)(F)c1ccc(-c2ccc3[nH]c4c(ccc5cc[nH]c54)c3c2)cc1]

The expected compound (227 mg; 0.65 mmol; yield=65%) is obtained in the form of a gray solid.

Melting point >250° C.

High resolution mass spectrum (ESI+) calculated for C$_{21}$H$_{14}$F$_3$N$_2$ (M+H)$^+$351.1109. found 351.1125.

IR (KBr): 3390, 3362, 1654, 1614 cm$^{-1}$ $^1$H NMR (400 MHz, DMSO-d$_6$): 6.60 (1H, dd, J$_1$=3.0 Hz, J$_2$=2.0 Hz); 7.39 (1H, d, J=8.5 Hz); 7.41 (1H, dd, J$_1$=3.0 Hz, J$_2$=2.5 Hz); 7.69 (1H, dd, J$_1$=8.5 Hz, J$_2$=2.0 Hz); 7.73 (1H, dd, J$_1$=8.5 Hz, J$_2$=0.5 Hz); 7.81 (2H, d, J=8.0 Hz); 7.84 (1H, d, J=8.5 Hz); 8.01 (2H, d, J=8.0 Hz); 8.47 (1H, d, J=1.5 Hz); 10.86-10.92 (1H, bs, NH); 11.06-11.10 (1H, bs, NH)

$^{13}$C NMR (100 MHz, DMSO-d$_6$): 102.9; 111.8; 112.2; 112.5; 117.7; 122.6; 123.9; 125.6 (2C, q, J$_{CF}$=4 Hz); 127.2 (2C) (CH); 116.3; 121.8; 124.6 (q, J$_{CF}$=272 Hz); 124.9; 126.5 (q, J$_{CF}$=32 Hz); 126.6; 127.1; 129.3; 138.3; 145.6 (C)

Example 24

7-(4-trifluoromethoxyphenyl)-1,10-dihydropyrrolo[2,3-a]carbazole

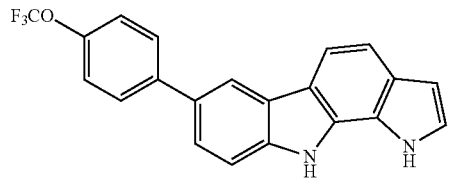 [SMILES: FC(F)(F)Oc1ccc(-c2ccc3[nH]c4c(ccc5cc[nH]c54)c3c2)cc1]

The expected compound (226 mg; 0.62 mmol; yield=62%) is obtained in the form of a gray solid.

Melting point >250° C.

High resolution mass spectrum (ESI+) calculated for C$_{21}$H$_{14}$F$_3$N$_2$O (M+H)$^+$367.1058. found 367.1044.

IR (KBr): 3401, 1652, 1514, 1464 cm$^{-1}$ $^1$H NMR (400 MHz, DMSO-d$_6$): 6.60 (1H, dd, J$_1$=3.0 Hz, J$_2$=2.0 Hz); 7.37 (1H, d, J=8.5 Hz); 7.40 (1H, t, J=2.5 Hz); 7.46 (2H, d, J=8.0 Hz); 7.62 (1H, dd, J$_1$=8.5 Hz, J$_2$=1.5 Hz); 7.70 (1H, d, J=8.5 Hz); 7.81 (1H, d, J=8.5 Hz); 7.87-7.91 (2H, m); 8.38 (1H, d, J=1.5 Hz); 10.85-10.90 (1H, bs, NH); 11.00-11.05 (1H, bs, NH)

$^{13}$C NMR (100 MHz, DMSO-d$_6$): 102.9; 111.7; 112.2; 112.4; 117.5; 121.4 (2C); 122.5; 123.8; 128.3 (CH); 116.3; 120.2 (q, J$_{CF}$=256 Hz); 121.8; 124.8; 126.5; 127.0; 129.6; 138.0; 141.0; 147.0 (q, J$_{CF}$=2 Hz) (C)

General Procedure for Preparing the Compounds of Examples 25-34

Stage A:

a suspension of substituted phenylhydrazine hydrochloride and of anhydrous sodium acetate in DME (20 mL) is stirred at room temperature for 1 hour. The compound of Preparation B (1.10 g; 4.0 mmol) and the ionic liquid of Preparation C (11.54 g; 28 mmol) are added. The solvent is evaporated off and the mixture is heated at 120° C. for 12 hours. After cooling, aqueous 0.5 M hydrochloric acid solution is added, followed by extraction with ethyl acetate. The organic fractions are washed with saturated aqueous NaCl solution, dried over MgSO$_4$ and filtered. The solution contains the expected product, and is used directly for the following oxidation step.

Stage B:

DDQ is added to this solution and the reaction mixture is stirred at room temperature overnight. The mixture is washed with saturated aqueous NaCl solution, dried over MgSO$_4$ and concentrated under vacuum.

Stage C:

the crude reaction product is dissolved in methanol (100 mL), aqueous 5 M KOH solution (25 mL) is added and the mixture is refluxed for 12 hours. After cooling, the solvent is removed under vacuum. The residue is neutralized with concentrated hydrochloric acid. After extracting with ethyl acetate, the organic fractions are combined and then washed with saturated aqueous NaCl solution, dried over MgSO$_4$ and evaporated. The solid obtained is purified by chromatography on silica gel.

Example 25

8-bromo-1,10-dihydropyrrolo[2,3-a]carbazole and

Example 26

6-bromo-1,10-dihydropyrrolo[2,3-a]carbazole

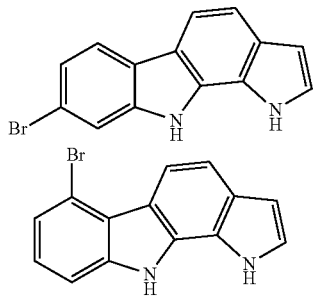

Stage A: 3-bromophenylhydrazine hydrochloride (1.00 g; 4.47 mmol), sodium acetate (367 mg; 4.47 mmol); stage B: DDQ (454 mg; 2.00 mmol); stage C: chromatography on silica gel (9/1 and then 8/2 cyclohexane/EtOAc) allows isolation of the compound of Example 25 (513 mg; 1.80 mmol; yield=45%) and the compound of Example 26 (342 mg; 1.20 mmol; yield=30%) in the form of gray solids.

Example 25

Melting point >250° C.

Mass spectrum (EI) m/z: 284/286, M$^+$

IR (ATR): 3397, 1649, 1607 cm$^{-1}$ $^1$H NMR (400 MHz, DMSO-d$_6$): 6.59 (1H, dd, J$_1$=3.0 Hz, J$_2$=2.0 Hz); 7.27 (1H, dd, J$_1$=8.5 Hz, J$_2$=2.0 Hz); 7.37 (1H, dd, J$_1$=8.5 Hz, J$_2$=0.5 Hz); 7.40 (1H, dd, J$_1$=3.0 Hz, J$_2$=2.5 Hz); 7.71 (1H, dd, J$_1$=8.5 Hz, J$_2$=0.5 Hz); 7.85 (1H, dd, J$_1$=2.0 Hz, J$_2$=0.5 Hz); 7.99 (1H, d, J=8.5 Hz); 10.94 (1H, bs, NH); 11.01 (1H, bs, NH)

$^{13}$C NMR (100 MHz, DMSO-d$_6$): 102.9; 111.9; 112.7; 113.9; 120.7; 121.3; 124.0 (CH); 115.6; 115.8; 121.6; 123.3; 126.6; 126.7; 139.1 (C)

Example 26

Melting point: 249-251° C.

High resolution mass spectrum (ESI+) calculated for C$_{14}$H$_{10}$$^{79}$BrN$_2$ (M+H)$^+$285.0027. found 285.0019.

IR (ATR): 3406, 3364, 1653, 1613 cm$^{-1}$ $^1$H NMR (400 MHz, DMSO-d$_6$): 6.62 (1H, dd, J$_1$=3.0 Hz, J$_2$=2.0 Hz); 7.23 (1H, t, J=8.0 Hz); 7.35 (1H, dd, J$_1$=7.5 Hz, J$_2$=0.5 Hz); 7.42 (1H, d, J=8.5 Hz); 7.44 (1H, t, J=2.5 Hz); 7.66 (1H, dd, J$_1$=8.0 Hz, J$_2$=0.5 Hz); 8.24 (1H, d, J=8.5 Hz); 10.90 (1H, bs, NH); 11.31 (1H, bs, NH)

$^{13}$C NMR (100 MHz, DMSO-d$_6$): 102.8; 110.6; 112.3; 113.4; 122.5; 124.3; 124.4 (CH); 114.2; 115.4; 121.4; 122.4; 126.6; 127.0; 139.4 (C)

Example 27

9-bromo-1,10-dihydropyrrolo[2,3-a]carbazole

Stage A: 2-bromophenylhydrazine hydrochloride (1.00 g; 4.47 mmol), sodium acetate (367 mg; 4.47 mmol); stage B: DDQ (636 mg; 2.80 mmol); stage C: chromatography on silica gel (from 9/1 to 7/3 cyclohexane/EtOAc) allows isolation of the expected compound (780 mg; 2.74 mmol; yield=68%) in the form of a white solid.

Melting point >250° C.

High resolution mass spectrum (ESI+) calculated for C$_{14}$H$_{10}$$^{79}$BrN$_2$ (M+H)$^+$285.0027. found 285.0012.

IR (ATR): 3314, 1636, 1622 cm$^{-1}$ $^1$H NMR (400 MHz, DMSO-d$_6$): 6.60 (1H, dd, J$_1$=3.0 Hz, J$_2$=2.0 Hz); 7.11 (1H, t, J=7.5 Hz); 7.40 (1H, dd, J$_1$=8.5 Hz, J$_2$=0.5 Hz); 7.45 (1H, dd, J$_1$=3.0 Hz, J$_2$=2.5 Hz); 7.52 (1H, dd, J$_1$=7.5 Hz, J$_2$=1.0 Hz); 7.73 (1H, dd, J$_1$=8.5 Hz, J$_2$=0.5 Hz); 8.07 (1H, dt, J$_1$=7.5 Hz, J$_2$=0.5 Hz); 10.79 (1H, bs, NH); 11.12 (1H, bs, NH)

$^{13}$C NMR (100 MHz, DMSO-d$_6$): 103.0; 112.3; 113.2; 118.6; 120.3; 124.2; 125.7 (CH); 103.6; 116.4; 121.7; 125.9; 126.5; 126.7; 136.5 (C)

Example 28

7-fluoro-1,10-dihydropyrrolo[2,3-a]carbazole

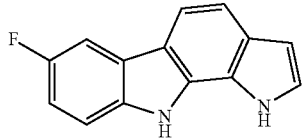 [SMILES: Fc1ccc2[nH]c3c(ccc4cc[nH]c43)c2c1]

Stage A: 4-fluorophenylhydrazine hydrochloride (1.30 g; 8.0 mmol), sodium acetate (656 mg; 8.0 mmol); stage B: DDQ (545 mg; 2.40 mmol); stage C: chromatography on silica gel (from 9/1 to 7/3 cyclohexane/EtOAc) allows isolation of the expected compound (702 mg; 3.13 mmol; yield=78%) in the form of a gray-green solid.

Melting point >250° C.

High resolution mass spectrum (ESI+) calculated for C$_{14}$H$_{10}$FN$_2$ (M+H)$^+$225.0828. found 225.0815.

IR (ATR): 3418, 3387, 1645, 1584 cm$^{-1}$ $^1$H NMR (400 MHz, DMSO-d$_6$): 6.58 (1H, dd, J$_1$=3.0 Hz, J$_2$=2.0 Hz); 7.12 (1H, ddd, J$_1$=9.5 Hz, J$_2$=9.0 Hz, J$_3$=2.5 Hz); 7.34 (1H, d, J=8.5 Hz); 7.39 (1H, t, J=2.5 Hz); 7.60 (1H, dd, J$_1$=8.5 Hz, J$_2$=4.5 Hz); 7.71 (1H, d, J=8.5 Hz); 7.84 (1H, dd, J$_1$=9.5 Hz, J$_2$=2.5 Hz); 10.89 (1H, bs, NH); 10.92 (1H, bs, NH)

$^{13}$C NMR (100 MHz, DMSO-d$_6$): 102.9; 104.5 (d, J$_{CF}$=24 Hz); 110.7 (d, J$_{CF}$=25 Hz); 112.0 (d, J$_{CF}$=9 Hz); 112.2 (2C); 123.9 (CH); 116.0 (d, J$_{CF}$=4 Hz); 121.6; 124.6 (d, J$_{CF}$=10 Hz); 126.5; 127.8; 134.6; 156.7 (d, J$_{CF}$=232) (C)

Example 29

9-fluoro-1,10-dihydropyrrolo[2,3-a]carbazole

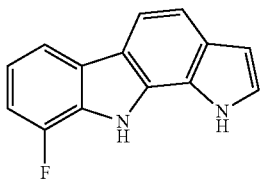 [SMILES: Fc1cccc2c1[nH]c1c2ccc2cc[nH]c21]

Stage A: 2-fluorophenylhydrazine hydrochloride (1.00 g; 6.15 mmol), sodium acetate (505 mg; 6.16 mmol); stage B: DDQ (450 mg; 1.98 mmol); stage C: chromatography on silica gel (from 9/1 to 7/3 cyclohexane/EtOAc) allows isolation of the expected compound (495 mg; 2.21 mmol; yield=55%) in the form of a beige-colored solid.

Melting point >250° C.

High resolution mass spectrum (ESI+) calculated for C$_{14}$H$_{10}$FN$_2$ (M+H)$^+$225.0828. found 225.0832.

IR (ATR): 3424, 3376, 1651, 1578 cm$^{-1}$ $^1$H NMR (400 MHz, DMSO-d$_6$): 6.60 (1H, dd, J$_1$=3.0 Hz, J$_2$=2.0 Hz); 7.08-7.19 (2H, m); 7.39 (1H, d, J=8.5 Hz); 7.42 (1H, t, J=2.5 Hz); 7.73 (1H, d, J=8.5 Hz); 7.88 (1H, d, J=7.5 Hz); 10.61 (1H, bs, NH); 11.40 (1H, bs, NH)

$^{13}$C NMR (100 MHz, DMSO-d$_6$): 102.9; 108.6 (d, J$_{CF}$=16 Hz); 112.1; 112.9; 115.3 (d, J$_{CF}$=3 Hz); 119.0 (d, J$_{CF}$=6 Hz); 124.1 (CH); 116.2 (d, J$_{CF}$=2.5 Hz); 121.7; 125.5 (d, J$_{CF}$=13 Hz); 126.7; 126.9; 128.0 (d, J$_{CF}$=6 Hz); 148.9 (d, J$_{CF}$=241 Hz) (C)

Example 30

6,8-dichloro-1,10-dihydropyrrolo[2,3-a]carbazole

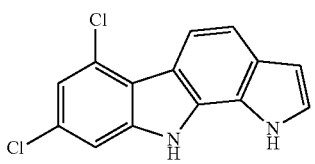 [SMILES: Clc1cc(Cl)c2c(c1)[nH]c1c2ccc2cc[nH]c21]

Stage A: 3,5-dichlorophenylhydrazine hydrochloride (1.00 g; 4.68 mmol), sodium acetate (384 mg; 4.68 mmol); stage B: DDQ (908 mg; 4.00 mmol); stage C: chromatography on silica gel (from 9/1 to 7/3 cyclohexane/EtOAc) allows isolation of the expected compound (971 mg; 3.53 mmol; yield=88%) in the form of a gray solid.

Melting point >250° C.

High resolution mass spectrum (ESI+) calculated for C$_{14}$H$_9{}^{35}$Cl$_2$N$_2$ (M+H)$^+$275.0143. found 275.0135.

IR (ATR): 3431, 3368, 1653, 1616 cm$^{-1}$ $^1$H NMR (400 MHz, DMSO-d$_6$): 6.62 (1H, dd, J$_1$=3.0 Hz, J$_2$=2.0 Hz); 7.27 (1H, d, J=1.5 Hz); 7.44 (1H, dd, J$_1$=8.5 Hz, J$_2$=0.5 Hz); 7.46 (1H, dd, J$_1$=3.0 Hz, J$_2$=2.5 Hz); 7.76 (1H, d, J=1.5 Hz); 8.05 (1H, d, J=8.5 Hz); 11.00 (1H, bs, NH); 11.42 (1H, bs, NH)

$^{13}$C NMR (100 MHz, DMSO-d$_6$): 102.9; 110.2; 113.3; 113.4; 118.9; 124.7 (CH); 114.4; 120.0; 121.2; 126.3; 126.9; 127.3; 127.5; 139.5 (C)

Example 31

1,10-dihydropyrrolo[2,3-a]carbazole-7-carbonitrile

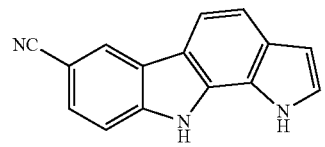 [SMILES: N#Cc1ccc2[nH]c3c(ccc4cc[nH]c43)c2c1]

Stage A: 4-cyanophenylhydrazine hydrochloride (1.36 g; 8.0 mmol), sodium acetate (656 mg; 8.0 mmol); stage B: DDQ (545 mg; 2.40 mmol); stage C: chromatography on silica gel (from 9/1 to 7/3 cyclohexane/EtOAc) allows isolation of the expected compound (517 mg; 2.24 mmol; yield=56%) in the form of a beige-colored solid.

Melting point >250° C.

High resolution mass spectrum (ESI+) calculated for C$_{15}$H$_{10}$N$_3$ (M+H)$^+$232.0875. found 232.0872.

IR (ATR): 3439, 3256, 2226, 1655, 1614 cm$^{-1}$ $^1$H NMR (400 MHz, DMSO-d$_6$): 6.63 (1H, dd, J$_1$=3.0 Hz, J$_2$=2.0 Hz); 7.42-7.46 (2H, m); 7.67 (1H, dd, J$_1$=8.5 Hz, J$_2$=1.5 Hz); 7.78 (1H, dd, J$_1$=8.5 Hz, J$_2$=0.5 Hz); 7.83 (1H, d, J=8.5 Hz); 8.61 (1H, m); 10.97 (1H, bs, NH); 11.53 (1H, bs, NH)

$^{13}$C NMR (100 MHz, DMSO-d$_6$): 103.0; 112.2; 112.3; 113.5; 124.2; 124.6; 126.5 (CH); 100.3; 115.4; 120.9; 121.4; 124.3; 127.2; 127.3; 140.1 (C)

Example 32

7-nitro-1,10-dihydropyrrolo[2,3-a]carbazole

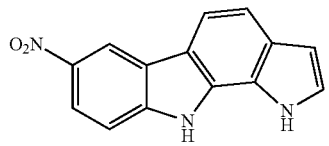 [SMILES: O=[N+]([O-])c1ccc2[nH]c3c(ccc4cc[nH]c43)c2c1]

Stage A: 4-nitrophenylhydrazine hydrochloride (1.52 g; 8.0 mmol), sodium acetate (656 mg; 8.0 mmol); stage B: DDQ (545 mg; 2.40 mmol); stage C: chromatography on silica gel (from 9/1 to 3/7 cyclohexane/EtOAc) allows isolation of the expected compound (450 mg; 1.79 mmol; yield=45%) in the form of a yellow-brown solid.

Melting point: 220° C. (decomposition)

High resolution mass spectrum (ESI+) calculated for C$_{14}$H$_{10}$N$_3$O$_2$ (M+H)$^+$252.0773. found 252.0763.

IR (ATR): 3406, 3298, 1655, 1616 cm$^{-1}$ $^1$H NMR (400 MHz, DMSO-d$_6$): 6.64 (1H, dd, J$_1$=3.0 Hz, J$_2$=2.0 Hz); 7.46-7.49 (2H, m); 7.79 (1H, d, J=9.0 Hz); 7.93 (1H, d, J=8.5 Hz); 8.22 (1H, dd, J$_1$=9.0 Hz, J$_2$=2.5 Hz); 9.06 (1H, d, J=2.5 Hz); 11.00 (1H, bs, NH); 11.74 (1H, bs, NH)

$^{13}$C NMR (100 MHz, DMSO-d$_6$): 103.1; 111.4; 112.4; 113.9; 115.9; 119.1; 124.8 (CH); 116.3; 121.5; 123.9; 127.6; 127.9; 140.0; 141.7 (CH)

Example 33

9-ethyl-1,10-dihydropyrrolo[2,3-a]carbazole

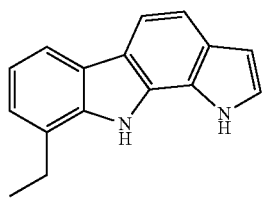 [SMILES: CCc1cccc2c1[nH]c1c2ccc2cc[nH]c21]

Stage A: 2-ethylphenylhydrazine hydrochloride (1.00 g; 5.79 mmol), sodium acetate (475 mg; 5.79 mmol); stage B: DDQ (454 mg; 2.00 mmol); stage C: chromatography on silica gel (from 9/1 to 7/3 cyclohexane/EtOAc) allows isolation of the expected compound (490 mg; 2.09 mmol; yield=52%) in the form of a gray solid.

Melting point: 256-258° C.

High resolution mass spectrum (ESI+) calculated for C$_{16}$H$_{15}$N$_2$ (M+H)$^+$235.1235. found 235.1228.

IR (ATR): 3426, 3416, 1649 cm$^{-1}$ $^1$H NMR (400 MHz, DMSO-d$_6$): 1.40 (3H, t, J=7.5 Hz); 2.99 (2H, q, J=7.5 Hz); 6.57 (1H, dd, J$_1$=3.0 Hz, J$_2$=2.0 Hz); 7.09 (1H, t, J=7.5 Hz); 7.13-7.16 (1H, m); 7.33 (1H, dd, J$_1$=8.5 Hz, J$_2$=0.5 Hz); 7.40 (1H, dd, J$_1$=3.0 Hz, J$_2$=2.5 Hz); 7.69 (1H, d, J$_1$=8.5 Hz, J$_2$=0.5 Hz); 7.87 (1H, d, J=7.5 Hz); 10.59 (1H, bs, NH); 10.85 (1H, bs, NH)

$^{13}$C NMR (100 MHz, DMSO-d$_6$): 14.2 (CH$_3$); 24.1 (CH$_2$); 102.8; 112.1 (2C); 116.9; 118.9; 122.2; 123.5 (CH); 116.5; 121.9; 123.8; 126.0 (2C); 126.3; 136.6 (C)

Example 34

9-(trifluoromethyl)-1,10-dihydropyrrolo[2,3-a]carbazole

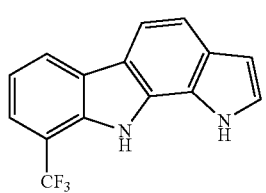 [SMILES: FC(F)(F)c1cccc2c1[nH]c1c2ccc2cc[nH]c21]

Stage A: 2-(trifluoromethyl)phenylhydrazine hydrochloride (1.00 g; 4.70 mmol), sodium acetate (386 mg; 4.71 mmol); stage B: DDQ (636 mg; 2.80 mmol); stage C: chromatography on silica gel (from 9/1 to 7/3 cyclohexane/EtOAc) allows isolation of the expected compound (550 mg; 2.01 mmol; yield=50%) in the form of a beige-colored solid.

Melting point >250° C.

High resolution mass spectrum (ESI+) calculated for C$_{15}$H$_{10}$F$_3$N$_2$ (M+H)$^+$275.0796. found 275.0781.

IR (ATR): 3453, 3385, 1649 cm$^{-1}$ $^1$H NMR (400 MHz, DMSO-d$_6$): 6.62 (1H, dd, J$_1$=3.0 Hz, J$_2$=2.0 Hz); 7.32 (1H, t, J=7.5 Hz); 7.44 (1H, d, J=8.5 Hz); 7.47 (1H, t, J=2.5 Hz); 7.63 (1H, d, J=7.5 Hz); 7.80 (1H, d, J=8.5 Hz); 8.37 (1H, d, J=8.0 Hz); 10.86 (1H, bs, NH); 11.34 (1H, bs, NH)

$^{13}$C NMR (100 MHz, DMSO-d$_6$): 102.9; 111.9; 113.4; 118.3; 120.3 (q, J$_{CF}$=4.5 Hz); 123.6; 124.3 (CH); 111.3 (q, J$_{CF}$=32 Hz); 115.3; 121.5; 125.1 (q, J$_{CF}$=271 Hz); 126.1; 126.9; 127.0; 133.2 (q, J$_{CF}$=2 Hz) (C)

Example 35

8-methyl-1:10-dihydropyrrolo[2,3-a]carbazole

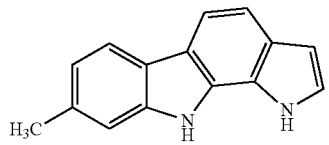 [SMILES: Cc1ccc2c(c1)[nH]c1c2ccc2cc[nH]c21]

Stage A: a mixture of 3-methylphenylhydrazine (1.00 g; 8.2 mmol), the compound of Preparation B (1.65 g; 6.0 mmol) and the ionic liquid of Preparation C (11.54 g; 28 mmol) is stirred at 120° C. for 12 hours. After cooling, aqueous 0.5 M HCl solution is added, followed by extraction with ethyl acetate. The combined organic fractions are washed with saturated aqueous NaCl solution, dried over MgSO$_4$ and filtered. The solution contains the expected product, and is used directly for the following oxidation step.

Stages B and C are performed in the same manner as for Examples 25 to 34.

Stage B: DDQ (953 mg; 4.20 mmol); stage C: chromatography on silica gel (from 9/1 to 7/3 cyclohexane/EtOAc) allows isolation of the expected compound (860 mg; 3.90 mmol; yield=65%) in the form of a gray solid.

Melting point >250° C.

Mass spectrum (EI) m/z: 220, M$^+$

IR (ATR): 3410, 3387, 1649, 1622 cm$^{-1}$ $^1$H NMR (400 MHz, DMSO-d$_6$): 2.48 (3H, s); 6.55 (1H, dd, J$_1$=3.0 Hz, J$_2$=2.0 Hz); 6.95-6.98 (1H, m); 7.30 (1H, d, J=8.5 Hz); 7.35 (1H, t, J=2.5 Hz); 7.39 (1H, m); 7.65 (1H, d, J=8.5 Hz); 7.89 (1H, d, J=8.0 Hz); 10.73 (1H, bs, NH); 10.76 (1H, bs, NH)

$^{13}$C NMR (100 MHz, DMSO-d$_6$): 21.6 (CH$_3$); 102.7; 111.2; 111.8; 111.9; 118.8; 120.1; 123.4 (CH); 116.2; 121.9 (2C); 125.9; 126.2; 132.6; 138.6 (C)

Example 36

7-(3-methoxyphenyl)-1,10-dihydropyrrolo[2,3-a]-carbazole-3-carbaldehyde

POCl$_3$ (90 µL, 0.97 mmol) is added slowly at 0° C. to anhydrous DMF (2 mL). The mixture is stirred at 0-10° C. for 45 minutes until a yellow solution is obtained. A solution of the compound of Example 18 (100 mg; 0.320 mmol) in DMF (1 ml) is then added. The mixture is heated at 120° C. for 24 hours. After cooling, aqueous 5% NaOH solution (20 mL) is added and the mixture is stirred at room temperature overnight. After extracting with ethyl acetate, the combined organic fractions are dried over MgSO$_4$ and evaporated, and the residue is purified by chromatography on silica gel (from 7/3 to 1/9 pentane/EtOAc) to give the expected compound (49 mg; 0.144 mmol; yield=45%) in the form of a light-brown solid.

Melting point 215° C. (decomposition)

High resolution mass spectrum (ESI+) calculated for $C_{22}H_{17}N_2O_2$ (M+H)$^+$341.1290. found 341.1305.

IR (KBr): 3325, 1619 cm$^{-1}$ $^1$H NMR (400 MHz, DMSO-d$_6$): 3.87 (3H, s, CH$_3$); 6.91 (1H, d, J=7.5 Hz); 7.31-7.42 (3H, m); 7.69 (1H, dd, J$_1$=8.5 Hz, J$_2$=1.5 Hz); 7.74 (1H, d, J=8.5 Hz); 7.95 (1H, d, J=8.5 Hz); 8.08 (1H, d, J=8.5 Hz); 8.31 (1H, d, J=3.0 Hz); 8.45 (1H, s); 10.04 (1H, s); 11.09-11.13 (1H, bs, NH); 11.88-11.92 (1H, bs, NH)

$^{13}$C NMR (100 MHz, DMSO-d$_6$): 55.1 (CH$_3$); 111.8; 112.0; 112.2 (2C); 115.3; 117.8; 119.1; 123.5; 129.8; 136.9 (CH); 118.6; 119.6; 122.8 (2C); 124.1; 126.5; 131.4; 138.2; 142.9; 159.7 (C); 185.3 (C=O)

General Procedure for Preparing the Compounds of Examples 37-52

POCl$_3$ (3 eq.) is added slowly at 0° C. to anhydrous DMF (2 mL). The solution is stirred at 0-10° C. for 45 minutes until a yellow solution is obtained, and is then added at 0° C. to a solution of the compounds of Examples 19-35 (100 mg) in DMF (1 mL), prepared in a 10 mL CEM tube. The tube is sealed and the mixture is heated at 100° C. under microwave irradiation (150 W) for 20 minutes. After cooling, the mixture is added to saturated aqueous NaHCO$_3$ solution (20 mL). After stirring for 30 minutes, the solid is filtered off and aqueous 5% NaOH solution (20 mL) is added thereto. The mixture is stirred at room temperature overnight. The solid is filtered off and then purified by chromatography on silica gel.

Example 37

7-(4-biphenyl)-1,10-dihydropyrrolo[2,3-a]carbazole-3-carbaldehyde

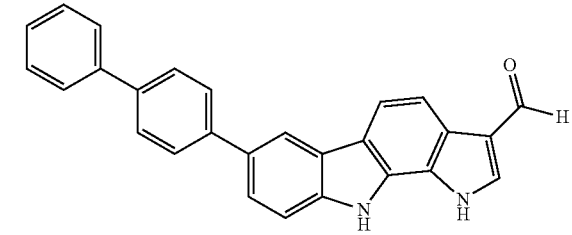 [SMILES: O=Cc1c[nH]c2c1ccc1c3cc(-c4ccc(-c5ccccc5)cc4)ccc3[nH]c12]

Chromatography on silica gel (from 7/3 to 1/9 pentane/EtOAc) allows isolation of the expected compound (32 mg; 0.083 mmol; yield=30%) in the form of a dark brown solid.

Melting point >250° C.

High resolution mass spectrum (ESI+) calculated for $C_{27}H_{19}N_2O$ (M+H)$^+$387.1497. found 387.1492.

IR (KBr): 3436, 1622 cm$^{-1}$ $^1$H NMR (400 MHz, DMSO-d$_6$): 7.36-7.41 (1H, m); 7.47-7.52 (2H, m); 7.73-7.81 (6H, m); 7.88-7.92 (2H, m); 7.96 (1H, d, J=8.5 Hz); 8.09 (1H, d, J=8.5 Hz); 8.31 (1H, d, J=3.0 Hz); 8.51 (1H, s); 10.05 (1H, s); 11.12-11.16 (1H, bs, NH); 11.90 (1H, bd, J=2.5 Hz, NH)

$^{13}$C NMR (100 MHz, DMSO-d$_6$): 112.0; 112.3; 115.3; 117.5; 123.3; 126.5 (2C); 127.1 (4C); 127.3; 129.0 (2C); 136.9 (CH); 118.6; 119.6; 122.8 (2C); 124.2; 126.5; 130.9; 138.0; 138.2; 139.8; 140.4 (C); 185.3 (C=O)

Example 38

7-phenyl-1,10-dihydropyrrolo[2,3-a]carbazole-3-carbaldehyde

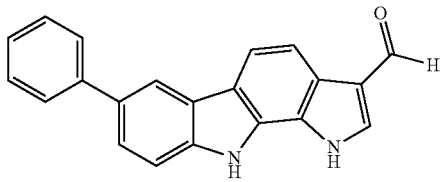 [SMILES: O=Cc1c[nH]c2c1ccc1c3cc(-c4ccccc4)ccc3[nH]c12]

Chromatography on silica gel (from 7/3 to 1/9 pentane/EtOAc) allows isolation of the expected compound (57 mg; 0.184 mmol; yield=52%) in the form of a dark brown solid.

Melting point 205° C. (decomposition)

High resolution mass spectrum (ESI+) calculated for $C_{21}H_{15}N_2O$ (M+H)$^+$311.1184. found 311.1201.

IR (KBr): 3260, 1622 cm$^{-1}$ $^1$H NMR (400 MHz, DMSO-d$_6$): 7.31-7.36 (1H, m); 7.46-7.51 (2H, m); 7.68 (1H, dd, J$_1$=8.5 Hz, J$_2$=2.0 Hz); 7.75 (1H, dd, J$_1$=8.5 Hz, J$_2$=0.5 Hz); 7.77-7.81 (2H, m); 7.95 (1H, d, J=8.5 Hz); 8.06 (1H, d, J=8.5 Hz); 8.31 (1H, d, J=3.0 Hz); 8.43 (1H, d, J=2.0 Hz); 10.04 (1H, s); 11.08-11.14 (1H, bs, NH); 11.86-11.93 (1H, bs, NH)

$^{13}$C NMR (100 MHz, DMSO-d$_6$): 111.9; 112.3; 115.3; 117.7; 123.4; 126.4; 126.7 (2C); 128.8 (2C); 136.9 (CH); 118.6; 119.6; 122.8 (2C); 124.2; 126.5; 131.5; 138.1; 141.4 (C); 185.4 (C=O)

Example 39

7-(4-fluorophenyl)-1,10-dihydropyrrolo[2,3-a]carbazole-3-carbaldehyde

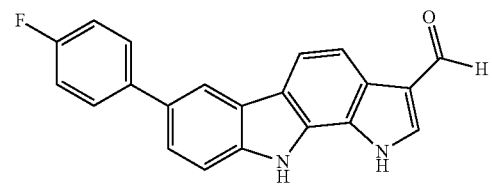 [SMILES: O=Cc1c[nH]c2c1ccc1c3cc(-c4ccc(F)cc4)ccc3[nH]c12]

Chromatography on silica gel (from 7/3 to 1/9 pentane/EtOAc) allows isolation of the expected compound (55 mg; 0.168 mmol; yield=50%) in the form of a light-brown solid.

Melting point >250° C.

High resolution mass spectrum (ESI+) calculated for $C_{21}H_{14}N_2OF$ (M+H)$^+$329. 1090. found 329. 1101.

IR (KBr): 3436, 3297, 1619 cm$^{-1}$ $^1$H NMR (400 MHz, DMSO-d$_6$): 7.27-7.34 (2H, m); 7.65 (1H, dd, J$_1$=8.5 Hz, J$_2$=2.0 Hz); 7.74 (1H, d, J=8.5 Hz); 7.78-7.84 (2H, m); 7.95 (1H, d, J=8.5 Hz); 8.06 (1H, d, J=8.5

Hz); 8.31 (1H, 5); 8.41 (1H, d, J=1.5 Hz); 10.04 (1H, 5); 11.10-11.15 (1H, bs, NH); 11.88-11.95 (1H, bs, NH)

$^{13}$C NMR (100 MHz, DMSO-d$_6$): 112.0; 112.3; 115.3; 115.6 (2C, d, J$_{CF}$=21 Hz); 117.7; 123.4; 128.5 (2C, d, J$_{CF}$=8 Hz); 136.9 (CH); 118.6; 119.6; 122.8 (2C); 124.2; 126.6; 130.6; 137.9 (d, J$_{CF}$=3 Hz); 138.1; 161.3 (d, J$_{CF}$=243 Hz); 185.4 (C=O)

Example 40

7-(2,4-difluorophenyl)-1,10-dihydropyrrolo[2,3-a]-carbazole-3-carbaldehyde

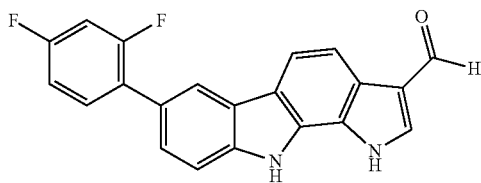 [SMILES: O=Cc1c[nH]c2c1ccc1c3cc(-c4ccc(F)cc4F)ccc3[nH]c12]

Chromatography on silica gel (from 7/3 to 1/9 pentane/EtOAc) allows isolation of the expected compound (48 mg; 0.139 mmol; yield=44%) in the form of a beige-colored solid.

Melting point 220° C. (decomposition)

High resolution mass spectrum (ESI+) calculated for C$_{21}$H$_{13}$F$_2$N$_2$O (M+H)$^+$347.0996. found 347.0996.

IR (KBr): 3264, 1645, 1616 cm$^{-1}$ $^1$H NMR (400 MHz, DMSO-d$_6$): 7.22 (1H, td, J$_1$=8.5 Hz, J$_2$=2.5 Hz); 7.37 (1H, ddd, J$_1$=11.5 Hz, J$_2$=9.5 Hz, J$_3$=2.5 Hz); 7.52 (1H, dt, J$_1$=8.5 Hz, J$_2$=2.0 Hz); 7.69 (1H, td, J$_1$=9.0 Hz, J$_2$=7.0 Hz); 7.76 (1H, d, J=8.5 Hz); 7.95 (1H, d, J=8.5 Hz); 8.02 (1H, d, J=8.5 Hz); 8.27 (1H, 5); 8.31 (1H, s); 10.04 (1H, s); 11.19-11.26 (1H, bs, NH); 11.90-12.01 (1H, bs, NH)

$^{13}$C NMR (100 MHz, DMSO-d$_6$): 104.3 (dd, J$_{CF1}$=27 Hz, J$_{CF2}$=26 Hz); 111.6; 111.8 (dd, J$_{CF1}$=21 Hz, J$_{CF2}$=4 Hz); 112.4; 115.2; 119.9 (d, J$_{CF}$=2 Hz); 125.2; 132.1 (dd, J$_{CF1}$=9 Hz, J$_{CF2}$=5 Hz); 136.9 (CH); 118.3; 119.6; 122.8 (2C); 123.8; 125.2; 126.1 (dd, J$_{CF1}$=14 Hz, J$_{CF2}$=4 Hz); 126.5; 138.1; 159.1 (dd, J$_{CF1}$=247 Hz, J$_{CF2}$=12 Hz); 161.1 (dd, J$_{CF1}$=246 Hz, J$_{CF2}$=12 Hz (C)); 185.3 (C=O)

Example 41

7-(4-trifluoromethylphenyl)-1,10-dihydropyrrolo-[2,3-a]carbazole-3-carbaldehyde

Chromatography on silica gel (from 7/3 to 1/9 pentane/EtOAc) allows isolation of the expected compound (70 mg; 0.185 mmol; yield=65%) in the form of a light-brown solid.

Melting point >250° C.

High resolution mass spectrum (ESI+) calculated for C$_{22}$H$_{14}$F$_3$N$_2$O (M+H)$^+$379.1058. found 379.1059.

IR (KBr): 3460, 3294, 1617 cm$^{-1}$ $^1$H NMR (400 MHz, DMSO-d$_6$): 7.76 (1H, dd, J$_1$=8.5 Hz, J$_2$=1.5 Hz); 7.80 (1H, dd, J$_1$=8.5 Hz, J$_2$=1.0 Hz); 7.83 (2H, d, J=8.0 Hz); 7.97 (1H, d, J=8.5 Hz); 8.03 (2H, d, J=8.0 Hz); 8.09 (1H, d, J=8.5 Hz); 8.32 (1H, s); 8.56 (1H, s); 10.04 (1H, s); 11.18-11.25 (1H, bs, NH); 11.88-11.97 (1H, bs, NH)

$^{13}$C NMR (100 MHz, DMSO-d$_6$): 112.2; 112.5; 115.3; 118.2; 123.5; 125.7 (2C, q, J$_{CF}$=4 Hz); 127.3 (2C); 137.0 (CH); 118.5; 119.6; 122.8; 122.9; 124.3; 124.6 (q, J$_{CF}$=272 Hz); 126.6; 126.7 (q, J$_{CF}$=32 Hz); 129.7; 138.7; 145.4 (C); 185.4 (C=O)

Example 42

7-(4-trifluoromethoxyphenyl)-1,10-dihydropyrrolo[2,3-a]carbazole-3-carbaldehyde

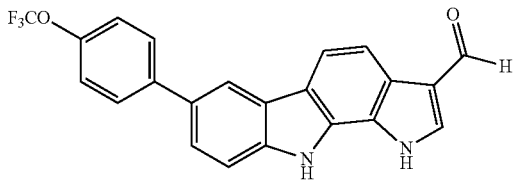 [SMILES: O=Cc1c[nH]c2c1ccc1c3cc(-c4ccc(OC(F)(F)F)cc4)ccc3[nH]c12]

Chromatography on silica gel (from 7/3 to 1/9 pentane/EtOAc) allows isolation of the expected compound (72 mg; 0.183 mmol; yield=67%) in the form of a beige-colored solid.

Melting point >250° C.

High resolution mass spectrum (ESI+) calculated for C$_{22}$H$_{14}$F$_3$N$_2$O$_2$ (M+H)$^+$395.1007. found 395.1017.

IR (KBr): 3276, 1620 cm$^{-1}$ $^1$H NMR (500 MHz, DMSO-d$_6$): 7.46 (2H, d, J=8.5 Hz); 7.69 (1H, dd, J$_1$=8.5 Hz, J$_2$=2.0 Hz); 7.75 (1H, d, J=8.5 Hz); 7.88-7.92 (2H, m); 7.95 (1H, d, J=8.5 Hz); 8.06 (1H, d, J=8.5 Hz); 8.31 (1H, d, J=3.0 Hz); 8.46 (1H, d, J=2.0 Hz); 10.03 (1H, s); 11.15-11.18 (1H, bs, NH); 11.93 (1H, bd, J=2.5 Hz, NH)

$^{13}$C NMR (125 MHz, DMSO-d$_6$): 112.1; 112.5; 115.4; 118.0; 121.5 (2C); 123.6; 128.5 (2C); 137.0 (CH); 118.6; 119.7; 120.3 (q, J$_{CF}$=256 Hz); 122.9; 123.0; 124.3; 126.7; 130.1; 138.4; 140.8; 147.2 (q, J$_{CF}$=2 Hz) (C); 185.5 (C=O)

Example 43

8-bromo-1,10-dihydropyrrolo[2,3-a]carbazole-3-carbaldehyde

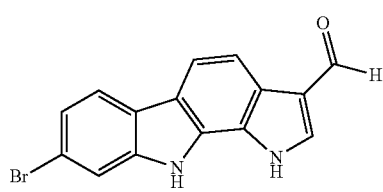

Chromatography on silica gel (from 7/3 to 1/9 cyclohexane/EtOAc) allows isolation of the expected compound (66 mg; 0.21 mmol; yield=60%) in the form of a brown solid.

Melting point >250° C.

Mass spectrum (EI) m/z: 312/314, M$^+$

IR (ATR): 3393, 3330-3160, 1624 cm$^{-1}$

¹H NMR (400 MHz, DMSO-d₆): 7.33 (1H, dd, J₁=8.5 Hz, J₂=2.0 Hz); 7.93 (1H, d, J=1.5 Hz); 7.94 (1H, d, J=8.5 Hz); 7.97 (1H, d, J=8.5 Hz); 8.07 (1H, d, J=8.5 Hz); 8.31 (1H, d, J=3.0 Hz); 10.03 (1H, s, CHO); 11.13 (1H, bs, NH); 11.96 (1H, bs, NH)

¹³C NMR (100 MHz, DMSO-d₆): 112.7; 114.3; 115.1; 121.2; 121.8; 137.0 (CH); 116.8; 117.8; 119.5; 122.6; 122.7; 123.0; 126.3; 139.4 (C); 185.4 (C=O)

Example 44

6-bromo-1,10-dihydropyrrolo[2,3-a]carbazole-3-carbaldehyde

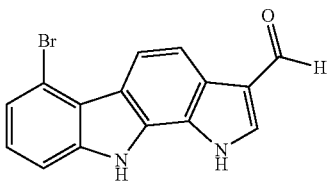 [SMILES: O=Cc1c[nH]c2c1ccc1c2[nH]c2cccc(Br)c21]

Chromatography on silica gel (from 7/3 to 1/9 cyclohexane/EtOAc) allows isolation of the expected compound (55 mg; 0.176 mmol; yield=50%) in the form of a brown solid.
Melting point >250° C.
Mass spectrum (EI) m/z: 312/314, M⁺
IR (ATR): 3300, 1620 cm⁻¹
¹H NMR (400 MHz, DMSO-d₆): 7.30 (1H, t, J=8.0 Hz); 7.41 (1H, d, J=7.5 Hz); 7.73 (1H, d, J=8.0 Hz); 7.99 (1H, d, J=8.5 Hz); 8.34 (1H, d, J=3.0 Hz); 8.46 (1H, d, J=8.5 Hz); 10.05 (1H, s, CHO); 11.46 (1H, bs, NH); 11.91 (1H, bs, NH)
¹³C NMR (100 MHz, DMSO-d₆): 111.0; 112.3; 116.3; 123.0; 125.2; 137.3 (CH); 114.6; 117.5; 119.5; 121.8; 122.4; 122.9; 126.6; 139.8 (C); 185.4 (C=O)

Example 45

9-bromo-1,10-dihydropyrrolo[2,3-a]carbazole-3-carbaldehyde

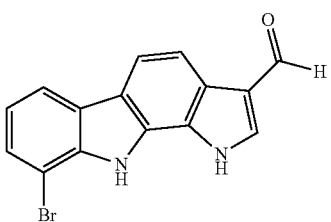 [SMILES: O=Cc1c[nH]c2c1ccc1c3cccc(Br)c3[nH]c12]

Chromatography on silica gel (from 7/3 to 1/9 cyclohexane/EtOAc) allows isolation of the expected compound (90 mg; 0.287 mmol; yield=82%) in the form of a brown solid.
Melting point >250° C.
High resolution mass spectrum (ESI+) calculated for C₁₅H₁₀⁷⁹BrN₂O (M+H)⁺312.9976. found 312.9991.
IR (ATR): 3400-3100, 1630 cm⁻¹
¹H NMR (400 MHz, DMSO-d₆): 7.16 (1H, t, J=7.5 Hz); 7.59 (1H, dd, J₁=7.5 Hz, J₂=1.0 Hz); 7.98 (2H, s); 8.15 (1H, d, J=7.5 Hz); 8.34 (1H, d, J=3.0 Hz); 10.05 (1H, s, CHO); 11.27 (1H, bs, NH); 11.69 (1H, bs, NH)

¹³C NMR (100 MHz, DMSO-d₆): 113.1; 115.4; 119.1; 120.6; 126.5; 137.1 (CH); 103.8; 118.5; 119.5; 122.7; 123.0; 125.2; 126.0; 136.7 (C); 185.5 (C=O)

Example 46

7-Fluoro-1,10-dihydropyrrolo[2,3-a]carbazole-3-carbaldehyde

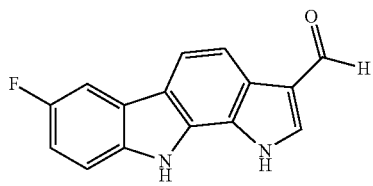 [SMILES: O=Cc1c[nH]c2c1ccc1c3cc(F)ccc3[nH]c12]

Chromatography on silica gel (from 3/7 to 1/9 cyclohexane/EtOAc) allows isolation of the expected compound (96 mg; 0.381 mmol; yield=85%) in the form of a brown solid.
Melting point >250° C.
High resolution mass spectrum (ESI+) calculated for C₁₅H₁₀FN₂O (M+H)⁺253.0777. found 253.0773.
IR (ATR): 3314, 1636, 1622 cm⁻¹
¹H NMR (400 MHz, DMSO-d₆): 7.20 (1H, ddd, J₁=9.5 Hz, J₂=9.0 Hz, J₃=2.5 Hz); 7.67 (1H, dd, J₁=9.0 Hz, J₂=4.5 Hz); 7.91 (1H, d, J=8.5 Hz); 7.92-7.95 (1H, m); 7.96 (1H, d, J=8.5 Hz); 8.30 (1H, d, J=3.0 Hz); 10.03 (1H, s, CHO); 11.07 (1H, bs, NH); 11.92 (1H, bs, NH)
¹³C NMR (100 MHz, DMSO-d₆): 105.0 (d, J_{CF}=24 Hz); 111.8 (d, J_{CF}=25 Hz); 112.2; 112.4 (d, J_{CF}=9 Hz); 115.4; 136.8 (CH); 118.2 (d, J_{CF}=4 Hz); 119.6; 122.7; 122.9; 124.1 (d, J_{CF}=10 Hz); 127.3; 135.0; 156.8 (d, J_{CF}=232 Hz) (C); 185.4 (C=O)

Example 47

9-Fluoro-1,10-dihydropyrrolo[2,3-a]carbazole-3-carbaldehyde

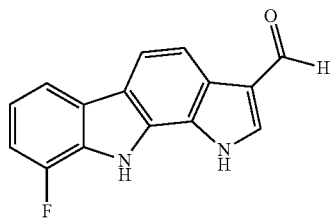 [SMILES: O=Cc1c[nH]c2c1ccc1c3cccc(F)c3[nH]c12]

Chromatography on silica gel (from 8/2 to 3/7 cyclohexane/EtOAc) allows isolation of the expected compound (80 mg; 0.317 mmol; yield=71%) in the form of a brown solid.
Melting point >250° C.
High resolution mass spectrum (ESI+) calculated for C₁₅H₁₀FN₂O (M+H)⁺253.0777. found 253.0792.
IR (ATR): 3450-3120, 1624 cm⁻¹
¹H NMR (400 MHz, DMSO-d₆): 7.17 (1H, dt, J₁=5.0 Hz, J₂=8.0 Hz); 7.24 (1H, ddd, J₁=11.0 Hz, J₂=8.0 Hz, J₃=1.0 Hz); 7.94-7.97 (2H, m); 7.98 (1H, d, J=8.5 Hz); 8.31 (1H, d, J=3.0 Hz); 10.05 (1H, s, CHO); 11.52 (1H, bs, NH); 11.57 (1H, bs, NH)

$^{13}$C NMR (100 MHz, DMSO-d$_6$): 109.4 (d, J$_{CF}$=16 Hz); 112.9; 115.2; 115.8 (d, J$_{CF}$=3 Hz); 119.5 (d, J$_{CF}$=6 Hz); 137.1 (CH); 118.3 (d, J$_{CF}$=2.5 Hz); 119.5; 122.8; 123.0; 125.9 (d, J$_{CF}$=13 Hz); 126.4; 127.4 (d, J$_{cF}$=6 Hz); 148.9 (d, J$_{CF}$=241 Hz) (C); 185.5 (C=O)

Example 48

6,8-dichloro-1,10-dihydropyrrolo[2,3-a]carbazole-3-carbaldehyde

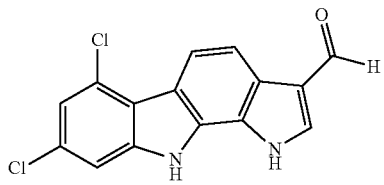 [SMILES: O=Cc1c[nH]c2c1ccc1c2[nH]c2cc(Cl)cc(Cl)c21]

Chromatography on silica gel (from 3/7 to 1/9 cyclohexane/EtOAc) allows isolation of the expected compound (52 mg; 0.172 mmol; yield=47%) in the form of a brown solid.

Melting point >250° C.

High resolution mass spectrum (ESI+) calculated for C$_{15}$H$_9$$^{35}$Cl$_2$N$_2$O (M+H)$^+$303.0092. found 303.0073.

IR (ATR): 3352, 1717, 1630 cm$^{-1}$ $^1$H NMR (400 MHz, DMSO-d$_6$): 7.34 (1H, d, J=1.5 Hz); 7.84 (1H, d, J=1.5 Hz); 8.01 (1H, d, J=8.5 Hz); 8.27 (1H, d, J=8.5 Hz); 8.36 (1H, d, J=3.0 Hz); 10.05 (1H, s, CHO); 11.54 (1H, bs, NH); 11.99 (1H, bs, NH).

$^{13}$C NMR (100 MHz, DMSO-d$_6$): 110.5; 113.2; 116.4; 119.3; 137.4 (CH); 116.5; 119.4; 119.5; 122.3; 123.2; 126.7; 126.9; 128.4; 139.8 (C); 185.4 (C=O).

Example 49

3-formyl-1,10-dihydropyrrolo[2,3-a]carbazole-7-carbonitrile

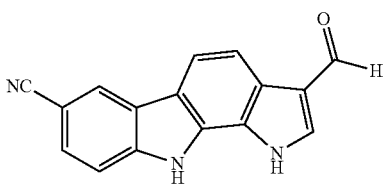 [SMILES: N#Cc1ccc2[nH]c3c(ccc4c(C=O)c[nH]c43)c2c1]

Chromatography on silica gel (from 3/7 to 1/9 cyclohexane/EtOAc) allows isolation of the expected compound (58.3 mg; 0.225 mmol; yield=52%) in the form of a brown solid.

Melting point >250° C.

High resolution mass spectrum (ESI+) calculated for C$_{16}$H$_{10}$N$_3$O (M+H)$^+$260.0824. found 260.0833.

IR (ATR): 3287, 3239, 2212, 1630, 1618 cm$^{-1}$ $^1$H NMR (400 MHz, DMSO-d$_6$): 7.74 (1H, dd, J$_1$=8.5 Hz, J$_2$=1.5 Hz); 7.85 (1H, dd, J$_1$=8.5 Hz, J$_2$=0.5 Hz); 8.01 (1H, d, J=8.5 Hz); 8.08 (1H, d, J=8.5 Hz); 8.35 (1H, d, J=3.0 Hz); 8.70 (1H, d, J=1.5 Hz); 10.05 (1H, s, CHO); 11.65 (1H, bs, NH); 11.97 (1H, bs, NH)

$^{13}$C NMR (100 MHz, DMSO-d$_6$): 112.7; 113.4; 115.4; 124.8; 127.3; 137.3 (CH); 100.8; 117.6; 119.5; 120.6; 122.5; 123.6; 123.7; 126.8; 140.5 (C); 185.5 (C=O)

Example 50

7-nitro-1,10-dihydropyrrolo[2,3-a]carbazole-3-carbaldehyde

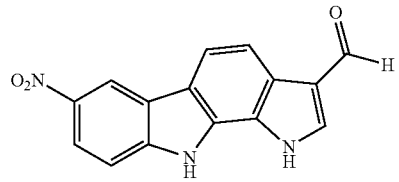 [SMILES: O=Cc1c[nH]c2c1ccc1c3cc([N+](=O)[O-])ccc3[nH]c12]

Chromatography on silica gel (from 3/7 to 1/9 cyclohexane/EtOAc) allows isolation of the expected compound (39 mg; 0.14 mmol; yield=35%) in the form of a yellow-brown solid.

Melting point >250° C.

High resolution mass spectrum (ESI+) calculated for C$_{15}$H$_{10}$N$_3$O$_3$ (M+H)$^+$280.0722. found 280.0714.

IR (ATR): 3350-3150, 1636, 1614 cm$^{-1}$ $^1$H NMR (400 MHz, DMSO-d$_6$): 7.85 (1H, d, J=9.0 Hz); 8.04 (1H, d, J=8.5 Hz); 8.19 (1H, d, J=8.5 Hz); 8.28 (1H, dd, J$_1$=9.0 Hz, J$_2$=2.5 Hz); 8.37 (1H, d, J=2.5 Hz); 9.14 (1H, d, J=2.0 Hz); 10.06 (1H, s, CHO); 11.87 (1H, bs, NH); 12.03 (1H, bs, NH)

$^{13}$C NMR (100 MHz, DMSO-d$_6$): 111.8; 113.8; 115.7; 116.5; 119.9; 137.5 (CH); 118.4; 119.5; 122.6; 123.3; 123.9; 127.5; 140.3; 142.0 (C); 185.5 (C=O)

Example 51

9-ethyl-1,10-dihydropyrrolo[2,3-a]carbazole-3-carbaldehyde

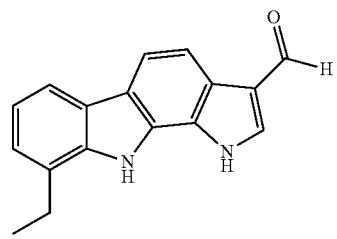 [SMILES: CCc1cccc2c1[nH]c1c2ccc2c(C=O)c[nH]c21]

Chromatography on silica gel (from 8/2 to 3/7 cyclohexane/EtOAc) allows isolation of the expected compound (56 mg; 0.213 mmol; yield=50%) in the form of a brown solid.

Melting point >250° C.

High resolution mass spectrum (ESI+) calculated for C$_{17}$H$_{15}$N$_2$O (M+H)$^+$263.1184. found 263.1169.

IR (ATR): 3450-3150, 1626 cm$^{-1}$ $^1$H NMR (400 MHz, DMSO-d$_6$): 1.40 (3H, t, J=7.5 Hz); 3.00 (2H, q, J=7.5 Hz); 7.14 (1H, t, J=7.5 Hz); 7.20-7.23 (1H, m); 7.90 (1H, d, J=8.5 Hz); 7.93 (1H, d, J=8.0 Hz); 7.93-7.96 (1H, m); 8.29 (1H, d, J=3.0 Hz); 10.03 (1H, s, CHO); 11.00 (1H, bs, NH); 11.54 (1H, bs, NH)

$^{13}$C NMR (100 MHz, DMSO-d$_6$): 14.1 (CH$_3$); 24.0 (CH$_2$); 112.1; 115.1; 117.3; 119.3; 123.1; 136.7 (CH); 118.7; 119.5; 122.3; 122.9; 123.2; 125.9; 126.2; 137.0 (C); 185.4 (C=O)

Example 52

8-methyl-1,10-dihydropyrrolo[2,3-a]carbazole-3-carbaldehyde

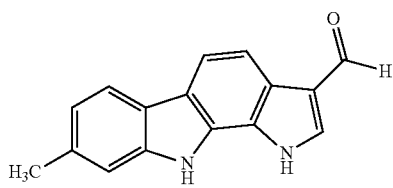 [SMILES: Cc1ccc2c(c1)[nH]c1c2ccc2c(C=O)c[nH]c21]

Chromatography on silica gel (from 7/3 to 1/9 cyclohexane/EtOAc) allows isolation of the expected compound (65 mg; 0.26 mmol; yield=58%) in the form of a brown solid.

Melting point: 250° C. (decomposition)

High resolution mass spectrum (ESI+) calculated for C$_{16}$H$_{13}$N$_2$O (M+H)$^+$249.1028. found 249.1026.

IR (ATR): 3379, 3341, 1634 cm$^{-1}$ $^1$H NMR (400 MHz, DMSO-d$_6$): 2.49 (3H, s); 7.02 (1H, d, J=8.0 Hz); 7.46 (1H, s); 7.89 (2H, s); 7.97 (1H, d, J=8.0 Hz); 8.27 (1H, d, J=3.0 Hz); 10.02 (1H, s, CHO); 11.88 (1H, bs, NH); 11.81 (1H, bs, NH)

$^{13}$C NMR (100 MHz, DMSO-d$_6$): 21.6 (CH$_3$); 111.5; 112.0; 114.8; 119.2; 120.6; 136.8 (CH); 118.5; 119.5; 121.3; 122.2; 122.8; 125.8; 133.7; 139.0 (C), 185.3 (C=O)

II) TEST OF ACTIVITY OF THE COMPOUNDS OF EXAMPLES 2, 3 And 5 ON 67 KINASES

The compounds of Example 2, i.e. 1,10-dihydropyrrolo[2,3-a]carbazole and of Example 3, i.e. 1,10-dihydropyrrolo[2,3-a]carbazole-3-carbaldehyde, and the compound of Example 5, i.e. 1,10-dihydropyrrolo[2,3-a]carbazole-3-carboxamide, were tested on the following 67 kinases:

MKK1, ERK 1, ERK 2, JNK1, JNK2, JNK3, p38a MAPK, p38b MAPK, p38g MAPK, p38s MAPK, ERK8, RSK1, RSK2, PDK1, PKBa, PKBb, SGK1, S6K1, PKA, ROCK2, PRK2, PKCa, PKC zeta, PKD1, MSK1, MNK1, MNK2, MAPKAP-K2, MAPKAP-K3, PRAK, CAMKKa, CAMKKb, CAMK1, SmMLCK, PHK, CHK1, CHK2, GSK3b, CDK2/cyclin A, PLK1, PLK1 (Okadaic acid), Aurora B, Aurora C, AMPK, MARK3, BRSK2, MELK, CK1, CK2, NEK2a, NEK6, NEK7, IKKb, PIM-1, PIM-2, PIM-3, SRPK1, MST2, EF2K, HIPK2, HIPK3, PAK-4, PAK5, PAK6, Src, Lck, CSK.

The results in terms of residual activity of the kinases after being placed in contact with the compounds of Examples 2, 3 and 5, at a concentration of 10 µM (10 µmol/L), are shown in Table 1 below.

The higher the residual activity of the kinase tested, the lower the inhibitory activity of the test compounds on the tested kinase.

| Compounds of Formula I | Kinases tested | | | | | |
|---|---|---|---|---|---|---|
| | % residual activity | % residual activity | % residual activity | % residual activity | % residual activity | % residual activity |
| | MKK1 | ERK1 | ERK2 | JNK1 | JNK2 | JNK3 |
| Example 2 | 87 | 108 | 94 | 102 | 118 | 108 |
| Example 3 | 50 | 87 | 92 | 102 | 128 | 113 |
| Example 5 | 80 | 71 | 93 | 106 | 115 | 104 |
| | p38a MAPK | p38b MAPK | p38g MAPK | p38s MAPK | ERK8 | RSK1 |
| Example 2 | 108 | 100 | 111 | 78 | 55 | 105 |
| Example 3 | 102 | 80 | 74 | 92 | 20 | 38 |
| Example 5 | 96 | 92 | 96 | 76 | 46 | 79 |
| | RSK2 | PDK1 | PKBa | PKBb | SGK1 | S6K1 |
| Example 2 | 129 | 86 | 120 | 107 | 82 | 89 |
| Example 3 | 124 | 76 | 96 | 98 | 64 | 38 |
| Example 5 | 97 | 67 | 97 | 103 | 71 | 72 |
| | PKA | ROCK2 | PRK2 | PKCa | PKC zeta | PKD1 |
| Example 2 | 95 | 86 | 95 | 111 | 91 | 83 |
| Example 3 | 60 | 25 | 31 | 84 | 83 | 28 |
| Example 5 | 80 | 48 | 54 | 80 | 78 | 19 |
| | MSK1 | MNK1 | MNK2 | MAPKAP-K2 | MAPKAP-K3 | PRAK |
| Example 2 | 90 | 69 | 95 | 118 | 89 | 97 |
| Example 3 | 71 | 27 | 55 | 84 | 69 | 72 |
| Example 5 | 91 | 19 | 57 | 92 | 75 | 85 |

|  | CAMKKa | CAMKKb | CAMK1 | SmMLCK | PHK | CHK1 |
|---|---|---|---|---|---|---|
| Example 2 | 76 | 93 | 29 | 86 | 90 | 123 |
| Example 3 | 42 | 56 | 71 | 60 | 33 | 97 |
| Example 5 | 75 | 79 | 80 | 69 | 43 | 113 |

|  | CHK2 | GSK3b | CDK2-Cyclin A | PLK1 | PLK1 (Okadaic acid) | AURORA B |
|---|---|---|---|---|---|---|
| Example 2 | 58 | 111 | 97 | 111 | 103 | 67 |
| Example 3 | 38 | 88 | 74 | 91 | 83 | 68 |
| Example 5 | 44 | 91 | 53 | 100 | 79 | 65 |

|  | AURORA C | AMPK | MARK3 | BRSK2 | MELK | CK1 |
|---|---|---|---|---|---|---|
| Example 2 | 85 | 80 | 116 | 58 | 93 | 107 |
| Example 3 | 79 | 59 | 88 | 22 | 61 | 103 |
| Example 5 | 61 | 85 | 73 | 32 | 80 | 96 |

|  | CK2 | NEK2a | NEK6 | NEK7 | IKKb | PIM-1 |
|---|---|---|---|---|---|---|
| Example 2 | 91 | 104 | 90 | 96 | 106 | 20 |
| Example 3 | 62 | 88 | 78 | 89 | 71 | 2 |
| Example 5 | 77 | 106 | 83 | 89 | 80 | 9 |

|  | PIM-2 | PIM-3 | SRPK1 | MST2 | EF2K | HIPK2 |
|---|---|---|---|---|---|---|
| Example 2 | 62 | 10 | 90 | 82 | 101 | 59 |
| Example 3 | 7 | 1 | 84 | 63 | 90 | 25 |
| Example 5 | 27 | 9 | 93 | 76 | 92 | 42 |

|  | HIPK3 | PAK4 | PAK5 | PAK6 | Src | Lck | CSK |
|---|---|---|---|---|---|---|---|
| Example 2 | 97 | 84 | 82 | 92 | 98 | 88 | 98 |
| Example 3 | 64 | 88 | 87 | 94 | 85 | 76 | 74 |
| Example 5 | 87 | 16 | 70 | 83 | 96 | 78 | 65 |

III) TEST OF ACTIVITY OF THE COMPOUNDS OF THE INVENTION ON THE KINASES PIM-1, PIM-2 AND PIM-3

The compounds according to the invention were then tested on the kinases PIM-1, PIM-2 and PIM-3.

The results in terms of percentage of residual activity after placing the compounds according to the invention in contact with each of the kinases PIM-1, PIM-2 and PIM-3 are given in Table 2 below.

The higher the residual activity, the lower the inhibitory activity of the test compounds.

TABLE 2

Percentage of residual activity at a concentration of product according to the invention of 10 µmol/L on the kinases PIM-1, PIM-2 and PIM-3

| Compounds | PIM-1 | PIM-2 | PIM-3 |
|---|---|---|---|
| Example 1 | 61 | 62 | 64 |
| Example 2 | 20 | 62 | 10 |
| Example 3 | 2 | 7 | 1 |
| Example 4 | 28 | 47 | 18 |
| Example 5 | 9 | 27 | 9 |
| Example 6 | 20 | 30 | 7 |
| Example 7 |  | N.D. |  |
| Example 8 | 44 | 47 | 33 |
| Example 9 | 35 | 50 | 21 |
| Example 10 | 54 | 51 | 39 |
| Example 11 | 39 | 78 | 25 |
| Example 12 | 24 | 53 | 16 |
| Example 13 | 41 | 27 | 21 |
| Example 14 | 51 | 52 | 61 |
| Example 15 | 12 | 46 | 8 |
| Example 16 | 6 | 57 | 6 |
| Example 17 |  | N.D. |  |
| Example 18 | 46 | 51 | 39 |
| Example 19 |  | N.D. |  |
| Example 20 |  | N.D. |  |
| Example 21 |  | N.D. |  |
| Example 22 |  | N.D. |  |
| Example 23 |  | N.D. |  |
| Example 24 |  | N.D. |  |
| Example 25 | 74 | 93 | 15 |
| Example 26 | 8 | 37 | 11 |
| Example 27 | 90 | N.I. | 43 |
| Example 28 | 35 | 84 | 20 |
| Example 29 | N.I. | N.I. | 43 |
| Example 30 | 10 | 36 | 14 |
| Example 31 | 9 | 26 | 4 |
| Example 32 | 9 | 23 | 11 |
| Example 33 | 28 | 96 | 23 |
| Example 34 | 85 | N.I. | 45 |
| Example 35 | 81 | N.I. | 13 |
| Example 36 | 17 | 31 | 12 |
| Example 37 | 39 | 70 | 48 |
| Example 38 | 16 | 53 | 15 |
| Example 39 | 15 | 55 | 15 |
| Example 40 | 6 | 32 | 6 |
| Example 41 | 28 | 52 | 23 |
| Example 42 | 29 | 70 | 31 |
| Example 43 | 44 | 39 | 15 |
| Example 44 | 2 | 6 | 5 |

TABLE 2-continued

Percentage of residual activity at a concentration of product according to the invention of 10 μmol/L on the kinases PIM-1, PIM-2 and PIM-3

| Compounds | PIM-1 | PIM-2 | PIM-3 |
|---|---|---|---|
| Example 45 | 3 | 28 | 9 |
| Example 46 | 4 | 21 | 5 |
| Example 47 | 5 | 11 | 3 |
| Example 48 | 8 | 34 | 6 |
| Example 49 | 92 | N.I. | 14 |
| Example 50 | N.I. | N.I. | 35 |
| Example 51 | 1 | 14 | 10 |
| Example 52 | 15 | 39 | 8 |

N.D.: not determined
N.I.: not inhibitory

The preferred compounds of the invention are those with a percentage of residual activity of less than or equal to 10%, i.e. the compounds of Examples 2, 3, 5, 6, 15, 16, 40, 44, 45, 46, 47, 48, 51 and 52.

IV) DETERMINATION OF THE MEAN INHIBITORY CONCENTRATION OF THE PREFERRED COMPOUNDS OF THE INVENTION

The mean inhibitory concentrations ($IC_{50}$) of certain preferred compounds of the invention were determined in the following manner: the $IC_{50}$ values were measured after performing the inhibition tests on the kinases PIM-1, PIM-2 and PIM-3 at ten different concentrations for each test compound, and the $IC_{50}$ value was determined from the dose-inhibition curves obtained.

The results are given in Table 3 below.

TABLE 3

$IC_{50}$ (μmol/L) on the kinases PIM-1, PIM-2 and PIM-3

|  | PIM-1 | PIM-2 | PIM-3 |
|---|---|---|---|
| Compound of Example 3 | 0.12 | 0.51 | 0.01 |
| Compound of Example 5 | 0.78 | N.D. | 0.21 |
| Compound of Example 6 | N.D. | N.D. | 0.17 |
| Compound of Example 15 | N.D. | N.D. | 0.44 |
| Compound of Example 16 | 0.57 | N.D. | 0.04 |
| Compound of Example 40 | 0.66 | N.D. | 0.20 |

N.D.: not determined

The invention claimed is:

1. A method of treating a disease associated with the activity of at least one kinase selected from the group consisting of PIM-1, PIM-2 and PIM-3 comprising administering to a subject in need thereof an amount of at least one compound of formula I below effective to inhibit at least one of PIM-1, PIM-2 or PIM 3:

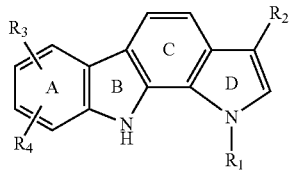

Formula I in which:
$R_1$ is H or a sulfophenyl group,
$R_2$, $R_3$ and $R_4$ are identical or different and represent, independently of each other, a hydrogen atom, a halogen atom or a group chosen among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —$NR_aR_b$, —$NR_aC(O)$-$T_1$, —C(N—OH)-$T_3$, —C(O)-$T_3$, —C(O)—C(O)-$T_3$, —C(O)—$NR_a$-$T_1$, —$NR_a$—C(O)-$T_1$, —O—C(O)-$T_1$, —C(O)—O-$T_1$, —O-$T_2$-$NR_aR_b$, —O-$T_2$-$OR_a$, —O-$T_2CO_2R_a$, —$NR_a$-$T_2$-$NR_aR_b$, —$NR_a$-$T_2$-$OR_a$, —$NR_a$-$T_2$-$CO_2R_a$ or —$S(O)_t$—$R_a$, —$S(O)_t$—$OR_a$, —$S(O)_t$—$NR_aR_b$, —$P(O)_t$—$R_a$, —$P(O)_t$—$OR_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$,
$R_5$ represents a halogen atom or a group chosen among linear or branched $C_1$ to $C_6$ alkyl, $C_6$ aryl, linear or branched $C_1$ to $C_6$ haloalkyl, —$OR_a$, —$NR_aR_b$, —$CO_2R_a$, —$C(O)R_a$ and —$C(O)NR_aR_b$, nitrile, nitro, —$NR_aC(O)$-$T_1$, $C_1$ to $C_6$ alkoxy, oxo, —$S(O)_t$—$R_a$, —$S(O)_t$—$OR_a$, —$S(O)_t$—$NR_aR_b$, —$P(O)_t$—$R_a$, —$P(O)_t$—$OR_a$,
$R_a$ and $R_b$ are identical or different and represent, independently of each other, a hydrogen atom or a group chosen among linear or branched $C_1$ to $C_6$ alkyl, linear or branched $C_1$ to $C_6$ haloalkyl and $C_6$ aryl, in which $R_a$+$R_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$,
$T_1$ represents a hydrogen atom, a halogen atom or a linear or branched $C_1$ to $C_6$ alkyl group, optionally substituted with a group chosen from —$OR_a$, —$NR_aR_b$, —$CO_2R_a$, —$C(O)R_a$ and —$C(O)NR_aR_b$,
$T_2$ represents a linear or branched ($C_1$-$C_6$)alkylidene chain,
$T_3$ represents a group chosen from -halogen, —$OR_a$, —$NR_aR_b$, —$CO_2R_a$, —$C(O)R_a$ and —$C(O)NR_aR_b$ in which $R_a$ and $R_b$ are as defined previously,
t represents an integer between 0 and 3 inclusive, and
A, B, C and D denote the rings constituting the compounds of formula I, and serve merely to identify each of these rings,
or a salt, optical isomer or racemic mixture of these compounds.

2. The method as claimed in claim 1, wherein the at least one compound has the formula I in which:
$R_1$ is H or a sulfophenyl group,
$R_2$ represents H or a group chosen among CHO, $(CH_2)_n$OH, $C(=O)NH_2$, $C(=O)$—$CF_3$, $(C=O)_2R_c$, $(CH_2)_2$ NEt$_2$, CH(OH)CH$_2$N(Et)$_2$, C(NOH)—(C=O)N(Et)$_2$, NO$_2$ and Br, with n=1 or 2 and R$_c$=OCH$_3$, OC$_2$H$_5$, N(C$_2$H$_5$)$_2$, and R$_3$ and R$_4$ are identical or different and are chosen, independently of each other, from H, a halogen atom, a 5- or 6-membered heteroaryl group comprising one or two heteroatoms chosen from O and N, linear or branched C$_1$ to C$_6$ alkyl, methoxy, nitro, nitrile, carboxyl, trifluoromethyl, trifluoromethoxy, SO$_2$R$_d$, C$_6$ aryl optionally substituted with a group chosen from a group (C=O)CH$_3$, phenyl, methoxy, trifluoromethoxy, trifluoromethyl and carboxyl or with 1 or 2 fluorine atoms, with R$_d$ chosen from a group OH, CH$_3$ or NH$_2$.

3. The method as claimed in claim 1, wherein the at least one compound has the formula I in which:

R$_1$ is H or a sulfophenyl group,

R$_2$ represents H or a group chosen among CHO, (CH$_2$)$_n$OH, C(=O)NH$_2$, C(=O)—CF$_3$, (C=O)$_2$R$_c$, (CH$_2$)$_2$NEt$_2$, CH(OH)CH$_2$N(Et)$_2$, C(NOH)—(C=O)N(Et)$_2$, NO$_2$ and Br, with n=1 or 2 and R$_c$ represents a group OCH$_3$ or OC$_2$H$_5$, or N(C$_2$H$_5$)$_2$, and R$_3$ and R$_4$ are identical or different and are chosen, independently of each other, from H, a halogen atom and a group from among methyl, ethyl, nitro, nitrile, trifluoromethyl, C$_6$ aryl optionally substituted with a group chosen from a group (C=O)CH$_3$, phenyl, methoxy, trifluoromethoxy and trifluoromethyl, or with 1 or 2 fluorine atoms.

4. The method as claimed in claim 1, wherein the at least one compound of formula I is chosen from the group consisting of 1,10-dihydropyrrolo[2,3-a]carbazole, 1,10-dihydropyrrolo[2,3-a]carbazole-3-carbaldehyde, 1,10-dihydropyrrolo[2,3-a]carbazole-3-carboxamide, 1-(1,10-dihydropyrrolo[2,3-a]carbazol-3-yl-2,2,2-trifluoroethanone, 7-bromo-1,10-dihydropyrrolo[2,3-a]carbazole, 7-bromo-1,10-dihydropyrrolo[2,3-a]carbazole-3-carbaldehyde, 7-(2,4-difluorophenyl)-1,10-dihydropyrrolo[2,3-a]carbazole-3-carbaldehyde, 6-bromo-1,10-dihydropyrrolo[2,3-a]carbazole-3-carbaldehyde, 9-bromo-1,10-dihydropyrrolo[2,3-a]carbazole-3-carbaldehyde, 7-fluoro-1,10-dihydropyrrolo[2,3-a]carbazole-3-carbaldehyde, 9-fluoro-1,10-dihydropyrrolo[2,3-a]carbazole-3-carbaldehyde, 6,8-dichloro-1,10-dihydropyrrolo[2,3-a]carbazole-3-carbaldehyde, 9-ethyl-1,10-dihydropyrrolo[2,3-a]carbazole-3-carbaldehyde and 8-methyl-1,10-dihydropyrrolo[2,3-a]carbazole-3-carbaldehyde.

5. The method as claimed in claim 1, wherein the at least one compound of formula I is chosen from the group consisting of 1,10-dihydropyrrolo[2,3-a]carbazole, 1,10-dihydropyrrolo[2,3-a]carbazole-3-carbaldehyde and 1,10-dihydropyrrolo[2,3-a]carbazole-3-carboxamide.

6. A process for synthesizing the compounds of formula I below:

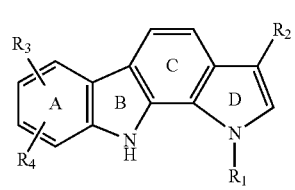

Formula I in which:

R$_1$ is H or a sulfophenyl group,

R$_2$, R$_3$ and R$_4$ are identical or different and represent, independently of each other, a hydrogen atom, a halogen atom or a group chosen among nitro, nitrile, hydroxyl, linear or branched C$_1$ to C$_6$ alkoxy optionally substituted with one or more groups R$_5$, C$_5$ to C$_6$ cycloalkoxy optionally substituted with one or more groups R$_5$, 5- or 6-membered heterocycloalkoxy optionally substituted with one or more groups R$_5$, —SH, linear or branched C$_1$ to C$_6$ alkylthio optionally substituted with one or more groups R$_5$, C$_6$ aryl optionally substituted with one or more groups R$_5$, C$_6$ aryloxy optionally substituted with one or more groups R$_5$, —NR$_a$R$_b$, —NR$_a$C(O)-T$_1$, —C(N—OH)-T$_3$, —C(O)-T$_1$, —C(O)—C(O)-T$_3$, —C(O)—NR$_a$-T$_1$, —NR$_a$—C(O)-T$_1$, —O—C(O)-T$_1$, —C(O)—O-T$_1$, —O-T$_2$-NR$_a$R$_b$, —O-T$_2$-OR$_a$, —O-T$_2$-CO$_2$R$_a$, —NR$_a$-T$_2$-NR$_a$R$_b$, —NR$_a$-T$_2$-OR$_a$, —NR$_a$-T$_2$-CO$_2$R$_a$ or —S(O)$_t$—R$_a$, —S(O)$_t$—OR$_a$, —S(O)$_t$—NR$_a$R$_b$, —P(O)$_t$—R$_a$, —P(O)$_t$—OR$_a$, linear or branched C$_1$ to C$_6$ alkyl optionally substituted with one or more groups R$_5$, linear or branched C$_1$ to C$_6$ alkenyl optionally substituted with one or more groups R$_5$, linear or branched C$_1$ to C$_6$ alkynyl optionally substituted with one or more groups R$_5$, 5- or 6-membered heteroaryl optionally substituted with one or more groups R$_5$, 5- or 6-membered heterocycloalkyl optionally substituted with one or more groups R$_5$, 5- or 6-membered heteroaryloxy optionally substituted with one or more groups R$_5$, R$_5$ represents a halogen atom or a group chosen among linear or branched C$_1$ to C$_6$ alkyl, C$_6$ aryl, linear or branched C$_1$ to C$_6$ haloalkyl, —OR$_a$, —NR$_a$R$_b$, —CO$_2$R$_a$, —C(O)R$_a$ and —C(O)NR$_a$R$_b$, nitrile, nitro, —NR$_a$C(O)-T$_1$, C$_1$ to C$_6$ alkoxy, oxo, —S(O)$_t$—R$_a$, —S(O)$_t$—OR$_a$, —S(O)$_t$—NR$_a$R$_b$, —P(O)$_t$—R$_a$, —P(O)$_t$—OR$_a$, R$_a$ and R$_b$ are identical or different and represent, independently of each other, a hydrogen atom or a group chosen among linear or branched C$_1$ to C$_6$ alkyl, linear or branched C$_1$ to C$_6$ haloalkyl and C$_6$ aryl, in which R$_a$+R$_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups R$_5$, T$_1$ represents a hydrogen atom, a halogen atom or a linear or branched C$_1$ to C$_6$ alkyl group, optionally substituted with a group chosen from —OR$_a$, —NR$_a$R$_b$, —CO$_2$R$_a$, —C(O)R$_a$ and —C(O)NR$_a$R$_b$, T$_2$ represents a linear or branched (C$_1$-C$_6$)alkylidene chain, $T_3$ represents a group chosen from -halogen, —$OR_a$, —$NR_aR_b$, —$CO_2R_a$, —$C(O)R_a$ and —$C(O)NR_aR_b$ in which $R_a$ and $R_b$ are as defined previously, t represents an integer between 0 and 3 inclusive, and A, B, C and D denote the rings constituting the compounds of formula I, and serve merely to identify each of these rings, comprising Fischer indolization of the compound 1-benzenesulfonyl-1,4,5,6-tetrahydro-7H-indol-7-one of formula II below:

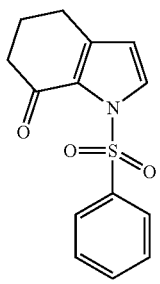

Formula II and phenylhydrazine or phenylhydrazine substituted on the phenyl with one or more groups $R_5$, in the presence of an ionic liquid, which is 2/1 zinc chloride-choline chloride of formula III below:

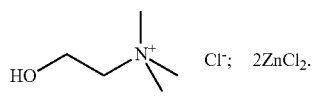

Formula III

7. A compound of formula I below:

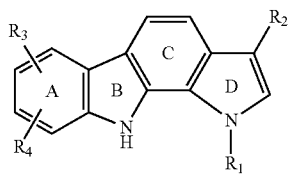

in which:

$R_1$ is H or a sulfophenyl group, $R_2$, $R_3$ and $R_4$ are identical or different and represent, independently of each other, a hydrogen atom, a halogen atom or a group chosen among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —$NR_aR_b$, —$NR_aC(O)$-$T_1$, —$C(N—OH)$-$T_3$, —$C(O)$-$T_1$, —$C(O)$—$C(O)$-$T_3$, —$C(O)$—$NR_a$-$T_1$, —$NR_a$—$C(O)$-$T_1$, —$O$—$C(O)$-$T_1$, —$C(O)$—$O$-$T_1$, —$O$-$T_2$-$NR_aR_b$, —$O$-$T_2$-$OR_a$, —$O$-$T_2$-$CO_2R_a$, —$NR_a$-$T_2$-$NR_aR_b$, —$NR_a$-$T_2$-$OR_a$, —$NR_a$-$T_2$-$CO_2R_a$ or —$S(O)_t$—$R_a$, —$S(O)_t$—$OR_a$, —$S(O)_t$—$NR_aR_b$, —$P(O)_t$—$R_a$, —$P(O)_t$—$OR_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$, $R_5$ represents a halogen atom or a group chosen among linear or branched $C_1$ to $C_6$ alkyl, $C_6$ aryl, linear or branched $C_1$ to $C_6$ haloalkyl, —$OR_a$, —$NR_aR_b$, —$CO_2R_a$, —$C(O)R_a$ and —$C(O)NR_aR_b$, nitrile, nitro, —$NR_aC(O)$-$T_1$, $C_1$ to $C_6$ alkoxy, oxo, —$S(O)_t$—$R_a$, —$S(O)_t$—$OR_a$, —$S(O)_t$—$NR_aR_b$, —$P(O)_t$—$R_a$, —$P(O)_t$—$OR_a$, $R_a$ and $R_b$ are identical or different and represent, independently of each other, a hydrogen atom or a group from among linear or branched $C_1$ to $C_6$ alkyl, linear or branched $C_1$ to $C_6$ haloalkyl and $C_6$ aryl, in which $R_a$+$R_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$, $T_1$ represents a hydrogen atom, a halogen atom or a linear or branched $C_1$ to $C_6$ alkyl group, optionally substituted with a group chosen from —$OR_a$, —$NR_aR_b$, —$CO_2R_a$, —$C(O)R_a$ and —$C(O)NR_aR_b$, $T_2$ represents a linear or branched ($C_1$-$C_6$)alkylidene chain, $T_3$ represents a group chosen from -halogen, —$OR_a$, —$NR_aR_b$, —$CO_2R_a$, —$C(O)R_a$ and —$C(O)NR_aR_b$ in which $R_a$ and $R_b$ are as defined previously, t represents an integer between 0 and 3 inclusive, and A, B, C and D denote the rings constituting the compounds of formula I, and serve merely to identify each of these rings, on condition that:

$R_1$, $R_2$, $R_3$ and $R_4$ are not all simultaneously H, when $R_1$ is a sulfophenyl group, then $R_2$, $R_3$ and $R_4$ are not all simultaneously H, and when $R_2$ is a carboxamide or formyl group, then $R_1$, $R_3$ and $R_4$ are not all simultaneously H.

8. The compound of formula I as claimed in claim 7, wherein in formula I:

$R_1$ is H or a sulfophenyl group, $R_2$ represents H, or a group from among CHO, $(CH_2)_nOH$, $C(=O)NH_2$, $C(=O)$—$CF_3$, $(C=O)_2R_c$, $(CH_2)_2NEt_2$, $CH(OH)CH_2N(Et)_2$, $C(NOH)$—$(C=O)N(Et)_2$, $NO_2$ and Br with n=1 or 2 and $R_c$=$OCH_3$, $OC_2H_5$ or $N(C_2H_5)_2$, and $R_3$ and $R_4$ are identical or different and are chosen, independently of each other, from H, a halogen atom, a 5- or 6-membered heteroaryl group comprising one or two heteroatoms chosen from O and N, linear or branched $C_1$ to $C_6$ alkyl, methoxy, nitro, nitrile, carboxyl, trifluoromethyl, trifluoromethoxy, $SO_2R_d$, $C_6$ aryl optionally substituted with a group chosen from a group ($C=O$)$CH_3$, phenyl, methoxy, trifluoromethoxy, trifluoromethyl and carboxyl or with 1 or 2 fluorine atoms, with $R_d$ chosen from a group OH, $CH_3$ or $NH_2$.

9. The compound as claimed in claim 7, wherein in formula I:

$R_1$ is H or a sulfophenyl group, $R_2$ represents H or a group from among CHO, $(CH_2)_nOH$, $C(=O)NH_2$, $C(O)-CF_3$, $(C=O)_2R_c$, $(CH_2)_2NEt_2$, $CH(OH)CH_2N(Et)_2$, $C(NOH)-(C=O)N(Et)_2$, $NO_2$ and Br, with n=1 or 2 and $R_c$ represents a group $OCH_3$, $OC_2H_5$ or $N(C_2H_5)_2$, and $R_3$ and $R_4$ are identical or different and are chosen, independently of each other, from H, a halogen atom and a group from among methyl, ethyl, nitro, nitrile, trifluoromethyl, $C_6$ aryl optionally substituted with a group chosen from a group $(C=O)CH_3$, phenyl, methoxy, trifluoromethoxy and trifluoromethyl, or with 1 or 2 fluorine atoms.

10. The compound of formula I as claimed in claim 7, selected from the group consisting of:

(1,10-dihydropyrrolo[2,3-a]carbazol-3-yl) methanol,
1-(1,10-dihydropyrrolo[2,3-c]carbazol-3-yl)-2,2,2-trifluoroethanone,
methyl 2-(1,10-dihydropyrrolo[2,3-a]carbazol-3-yl)-2-oxoacetate,
ethyl 2-(1,10-dihydropyrrolo[2,3-a]carbazol-3-yl)-2-oxoacetate,
2-(1,10-dihydropyrrolo[2,3-a]carbazol-3-yl) ethanol,
2-(1,10-dihydropyrrolo[2,3-c]carbazol-3-yl)-N,N-diethyl-2-oxoacetamide,
2-(1,10-dihydropyrrolo[2,3-c]carbazol-3-yl)-N,N-diethylethanamine,
1-(1,10-dihydropyrrolo[2,3-c]carbazol-3-yl)-2-diethylaminoethanol,
2-(1,10-dihydropyrrolo[2,3-c]carbazol-3-yl)-N,N-diethyl-2-hydroxyiminoethanamide,
1-benzenesulfonyl-7-bromo-1,10-dihydropyrrolo[2,3-a]carbazole,
7-bromo-1,10-dihydropyrrolo[2,3-a]carbazole,
7-bromo-1,10-dihydropyrrolo[2,3-a]carbazole-3-carbaldehyde,
7-(4-acetylphenyl)-1,10-dihydropyrrolo[2,3-a]carbazole,
7-(3-methoxyphenyl)-1,10-dihydropyrrolo[2,3-a]carbazole,
7-(4-biphenyl)-1,10-dihydropyrrolo[2,3-a]carbazole,
7-phenyl-1,10-dihydropyrrolo[2,3-a]carbazole,
7-(4-fluorophenyl)-1,10-dihydropyrrolo[2,3-a]carbazole,
7-(2,4-difluorophenyl)-1,10-dihydropyrrolo[2,3-a]carbazole,
7-(4-trifluoromethylphenyl)-1,10-dihydropyrrolo[2,3-a]carbazole,
7-(4-trifluoromethoxyphenyl)-1,10-dihydropyrrolo[2,3-a]carbazole,
8-bromo-1,10-dihydropyrrolo[2,3-a]carbazole,
6-bromo-1,10-dihydropyrrolo[2,3-a]carbazole,
9-bromo-1,10-dihydropyrrolo[2,3-a]carbazole,
7-fluoro-1,10-dihydropyrrolo[2,3-a]carbazole,
9-fluoro-1,10-dihydropyrrolo[2,3-a]carbazole,
6,8-dichloro-1,10-dihydropyrrolo[2,3-a]carbazole,
1,10-dihydropyrrolo[2,3-a]carbazole-7-carbonitrile,
7-nitro-1,10-dihydropyrrolo[2,3-a]carbazole,
9-ethyl-1,10-dihydropyrrolo[2,3-a]carbazole,
9-(trifluoromethyl)-1,10-dihydropyrrolo[2,3-a]carbazole,
8-methyl-1,10-dihydropyrrolo[2,3-a]carbazole,
7-(3-methoxyphenyl)-1,10-dihydropyrrolo[2,3-a]carbazole-3-carbaldehyde,
7-(4-biphenyl)-1,10-dihydropyrrolo[2,3-a]carbazole-3-carbaldehyde,
7-phenyl-1,10-dihydropyrrolo[2,3-a]carbazole-3-carbaldehyde,
7-(4-fluorophenyl)-1,10-dihydropyrrolo[2,3-a]carbazole-3-carbaldehyde,
7-(2,4-difluorophenyl)-1,10-dihydropyrrolo[2,3-a]carbazole-3-carbaldehyde,
7-(4-trifluoromethylphenyl)-1,10-dihydropyrrolo[2,3-a]carbazole-3-carbaldehyde,
7-(4-trifluoromethoxyphenyl)-1,10-dihydropyrrolo[2,3-a]carbazole-3-carbaldehyde,
8-bromo-1,10-dihydropyrrolo[2,3-a]carbazole-3-carbaldehyde,
6-bromo-1,10-dihydropyrrolo[2,3-a]carbazole-3-carbaldehyde,
9-bromo-1,10-dihydropyrrolo[2,3-a]carbazole-3-carbaldehyde,
7-fluoro-1,10-dihydropyrrolo[2,3-a]carbazole-3-carbaldehyde,
9-fluoro-1,10-dihydropyrrolo[2,3-a]carbazole-3-carbaldehyde,
6,8-dichloro-1,10-dihydropyrrolo[2,3-a]carbazole-3-carbaldehyde,
3-formyl-1,10-dihydropyrrolo[2,3-a]carbazole-7-carbonitrile,
7-nitro-1,10-dihydropyrrolo[2,3-a]carbazole-3-carbaldehyde,
9-ethyl-1,10-dihydropyrrolo[2,3-a]carbazole-3-carbaldehyde, and
8-methyl-1,10-dihydropyrrolo[2,3-a]carbazole-3-carbaldehyde.

11. The compound of formula I as claimed in claim 7, selected from the group consisting of 1,10-dihydropyrrolo[2,3-a]carbazol-3-yl-2,2,2-trifluoroethanone,
7-bromo-1,10-dihydropyrrolo[2,3-a]carbazole,
7-bromo-1,10-dihydropyrrolo[2,3-a]carbazole-3-carbaldehyde,
7-(2,4-difluorophenyl)-1,10-dihydropyrrolo[2,3-a]carbazole-3-carbaldehyde,
6-bromo-1,10-dihydropyrrolo[2,3-a]carbazole-3-carbaldehyde,
9-bromo-1,10-dihydropyrrolo[2,3-a]carbazole-3-carbaldehyde,
7-fluoro-1,10-dihydropyrrolo[2,3-a]carbazole-3-carbaldehyde,
9-fluoro-1,10-dihydropyrrolo[2,3-a]carbazole-3-carbaldehyde,
6,8-dichloro-1,10-dihydropyrrolo[2,3-a]carbazole-3-carbaldehyde,
9-ethyl-1,10-dihydropyrrolo[2,3-a]carbazole-3-carbaldehyde and
8-methyl-1,10-dihydropyrrolo[2,3-a]carbazole-3-carbaldehyde.

12. A method of treating prostate cancer, leukemia, lymphoma and ovarian cancer comprising administering to a subject in need thereof an effective amount of at least one compound of formula I below:

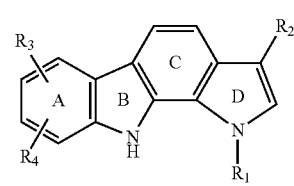

Formula I in which:
R₁ is H or a sulfophenyl group,
R₂, R₃ and R₄ are identical or different and represent, independently of each other, a hydrogen atom, a halogen atom or a group chosen among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —NR$_a$R$_b$, —NR$_a$C(O)-T$_1$, —C(N—OH)-T$_3$, —C(O)-T$_1$, —C(O)—C(O)-T$_3$, —C(O)—NR$_a$-T$_1$, —NR$_a$—C(O)-T$_1$, —O—C(O)-T$_1$, —C(O)—O-T$_1$, —O-T$_2$-NR$_a$R$_b$, —O-T$_2$-OR$_a$, —O-T$_2$CO$_2$R$_a$, —NR$_a$-T$_2$-NR$_a$R$_b$, —NR$_a$-T$_2$-OR$_a$, —NR$_a$-T$_2$-CO$_2$R$_a$ or —S(O)$_t$—R$_a$, —S(O)$_t$—OR$_a$, —S(O)$_t$—NR$_a$R$_b$, —P(O)$_t$—R$_a$, —P(O)$_t$—OR$_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$,
R₅ represents a halogen atom or a group chosen among linear or branched $C_1$ to $C_6$ alkyl, $C_6$ aryl, linear or branched $C_1$ to $C_6$ haloalkyl, —OR$_a$, —NR$_a$R$_b$, —CO$_2$R$_a$, —C(O)R$_a$ and —C(O)NR$_a$R$_b$, nitrile, nitro, —NR$_a$C(O)-T$_1$, $C_1$ to $C_6$ alkoxy, oxo, —S(O)$_t$—R$_a$, —S(O)$_t$—OR$_a$, —S(O)$_t$—NR$_a$R$_b$, —P(O)$_t$—R$_a$, —P(O)$_t$—OR$_a$,
R$_a$ and R$_b$ are identical or different and represent, independently of each other, a hydrogen atom or a group chosen among linear or branched $C_1$ to $C_6$ alkyl, linear or branched $C_1$ to $C_6$ haloalkyl and $C_6$ aryl, in which R$_a$+R$_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$,
T$_1$ represents a hydrogen atom, a halogen atom or a linear or branched $C_1$ to $C_6$ alkyl group, optionally substituted with a group chosen from —OR$_a$, —NR$_a$R$_b$, —CO$_2$R$_a$, —C(O)R$_a$ and —C(O)NR$_a$R$_b$,
T$_2$ represents a linear or branched ($C_1$-$C_6$)alkylidene chain,
T$_3$ represents a group chosen from -halogen, —OR$_a$, —NR$_a$R$_b$, —CO$_2$R$_a$, —C(O)R$_a$ and —C(O)NR$_a$R$_b$ in which R$_a$ and R$_b$ are as defined previously,
t represents an integer between 0 and 3 inclusive, and
A, B, C and D denote the rings constituting the compounds of formula I, and serve merely to identify each of these rings,
or a salt, optical isomer or racemic mixture of these compounds.

13. A method of treating a disease associated with the activity of at least one kinase selected from the group consisting of PIM-1, PIM-2 and PIM-3 comprising administering to a subject in need thereof an amount of at least one compound of formula I below effective to inhibit at least one of PIM-1, PIM-2 or PIM-3:

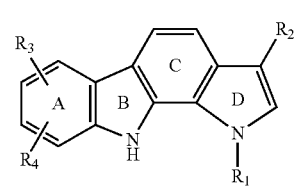

Formula I in which:
R₁ is H or a sulfophenyl group,
R₂ is a formyl group,
R₃ and R₄ are identical or different and represent, independently of each other, a hydrogen atom, a halogen atom or a group chosen among nitro, nitrile, hydroxyl, linear or branched $C_1$ to $C_6$ alkoxy optionally substituted with one or more groups $R_5$, $C_5$ to $C_6$ cycloalkoxy optionally substituted with one or more groups $R_5$, 5- or 6-membered heterocycloalkoxy optionally substituted with one or more groups $R_5$, —SH, linear or branched $C_1$ to $C_6$ alkylthio optionally substituted with one or more groups $R_5$, $C_6$ aryl optionally substituted with one or more groups $R_5$, $C_6$ aryloxy optionally substituted with one or more groups $R_5$, —NR$_a$R$_b$, —NR$_a$C(O)-T$_1$, —C(N—OH)-T$_3$, —C(O)-T$_1$, —C(O)—C(O)-T$_3$, —C(O)—NR$_a$-T$_1$, —NR$_a$—C(O)-T$_1$, —O—C(O)-T$_1$, —C(O)—O-T$_1$, —O-T$_2$-NR$_a$R$_b$, —O-T$_2$-OR$_a$, —O-T$_2$CO$_2$R$_a$, —NR$_a$-T$_2$-NR$_a$R$_b$, —NR$_a$-T$_2$-OR$_a$, —NR$_a$-T$_2$-CO$_2$R$_a$ or —S(O)$_t$—R$_a$, —S(O)$_t$—OR$_a$, —S(O)$_t$—NR$_a$R$_b$, —P(O)$_t$—R$_a$, —P(O)$_t$—OR$_a$, linear or branched $C_1$ to $C_6$ alkyl optionally substituted with one or more groups $R_5$, linear or branched $C_1$ to $C_6$ alkenyl optionally substituted with one or more groups $R_5$, linear or branched $C_1$ to $C_6$ alkynyl optionally substituted with one or more groups $R_5$, 5- or 6-membered heteroaryl optionally substituted with one or more groups $R_5$, 5- or 6-membered heterocycloalkyl optionally substituted with one or more groups $R_5$, 5- or 6-membered heteroaryloxy optionally substituted with one or more groups $R_5$,
R₅ represents a halogen atom or a group chosen among linear or branched $C_1$ to $C_6$ alkyl, $C_6$ aryl, linear or branched $C_1$ to $C_6$ haloalkyl, —OR$_a$, —NR$_a$R$_b$, —CO$_2$R$_a$, —C(O)R$_a$ and —C(O)NR$_a$R$_b$, nitrile, nitro, —NR$_a$C(O)-T$_1$, $C_1$ to $C_6$ alkoxy, oxo, —S(O)$_t$—R$_a$, —S(O)$_t$—OR$_a$, —S(O)$_t$—NR$_a$R$_b$, —P(O)$_t$—R$_a$, —P(O)$_t$—OR$_a$,
R$_a$ and R$_b$ are identical or different and represent, independently of each other, a hydrogen atom or a group chosen among linear or branched $C_1$ to $C_6$ alkyl, linear or branched $C_1$ to $C_6$ haloalkyl and $C_6$ aryl, in which R$_a$+R$_b$ form, together with the nitrogen atom to which they are attached, a saturated or unsaturated, monocyclic or bicyclic heterocycle of 5 to 10 atoms, optionally containing in the ring systems a second heteroatom chosen from oxygen and nitrogen, and being optionally substituted with one or more groups $R_5$,
T$_1$ represents a hydrogen atom, a halogen atom or a linear or branched $C_1$ to $C_6$ alkyl group, optionally substituted with a group chosen from —$OR_a$, —$NR_aR_b$, —$CO_2R_a$, —$C(O)R_a$ and —$C(O)NR_aR_b$, $T_2$ represents a linear or branched ($C_1$-$C_6$)alkylidene chain, $T_3$ represents a group chosen from -halogen, —$OR_a$, —$NR_aR_b$, —$CO_2R_a$, —$C(O)R_a$ and —$C(O)NR_aR_b$ in which $R_a$ and $R_b$ are as defined previously, t represents an integer between 0 and 3 inclusive, and A, B, C and D denote the rings constituting the compounds of formula I, and serve merely to identify each of these rings, or a salt, optical isomer or racemic mixture of these compounds.

\* \* \* \* \*